(12) United States Patent
Lindsey et al.

(10) Patent No.: US 8,278,439 B2
(45) Date of Patent: Oct. 2, 2012

(54) SYNTHESIS OF PHOSPHONO-SUBSTITUTED PORPHYRIN COMPOUNDS FOR ATTACHMENT TO METAL OXIDE SURFACES

(75) Inventors: Jonathan S. Lindsey, Raleigh, NC (US); Robert S. Loewe, Morrisville, NC (US); Kannan Muthukumaran, Raleigh, NC (US); Arounaguiry Ambroise, Cary, NC (US)

(73) Assignees: North Carolina State University, Raleigh, NC (US); ZettaCore, Inc., Englewood, CO (US)

( * ) Notice: Subject to any disclaimer, the term of this patent is extended or adjusted under 35 U.S.C. 154(b) by 0 days.

(21) Appl. No.: 13/299,894

(22) Filed: Nov. 18, 2011

(65) Prior Publication Data

US 2012/0065391 A1 Mar. 15, 2012

Related U.S. Application Data

(62) Division of application No. 12/473,438, filed on May 28, 2009, now Pat. No. 8,080,653, which is a division of application No. 11/937,808, filed on Nov. 9, 2007, now Pat. No. 7,553,977, which is a division of application No. 11/553,542, filed on Oct. 27, 2006, now Pat. No. 7,314,941, which is a division of application No. 10/698,255, filed on Oct. 31, 2003, now Pat. No. 7,148,361.

(51) Int. Cl.
*C07D 207/00* (2006.01)
*C07F 9/02* (2006.01)

(52) U.S. Cl. ......... 540/145; 548/400; 548/405; 548/413

(58) Field of Classification Search .................. 540/145; 548/400, 405, 413
See application file for complete search history.

(56) References Cited

U.S. PATENT DOCUMENTS

| 6,420,648 | B1 | 7/2002 | Lindsey | |
|---|---|---|---|---|
| 6,559,374 | B2 | 5/2003 | Lindsey et al. | |
| 6,603,070 | B2 | 8/2003 | Lindsey et al. | |
| 6,642,376 | B2 | 11/2003 | Lindsey et al. | |
| 7,148,361 | B2 | 12/2006 | Lindsey et al. | |
| 7,314,941 | B2 | 1/2008 | Lindsey et al. | |
| 7,553,977 | B2 * | 6/2009 | Lindsey et al. | 548/400 |
| 7,595,407 | B2 * | 9/2009 | Lindsey et al. | 548/405 |
| 2003/0096978 | A1 | 5/2003 | Lindsey et al. | |

OTHER PUBLICATIONS

Balasubramanian T et al. Rational synthesis of beta-substituted chlorin building blocks. J. Org. Chem. 2000; 65: 7919-7929.
Strachan J-P et al. Rational synthesis of meso-substituted chlorin building blocks. J. Org. Chem. 2000; 65: 3160-3172.
Muthukumaran K et al. Porphyrins bearing arylphosphonic acid tethers for attachment to oxide surfaces. J. Org. Chem. 2004; 69(5): 1444-1452.
Lindsey et al., "Investigation of the Synthesis of Ortho-Substituted Tetraphenylphorphyrins," Apr. 21, 1988, J. Org. Chem., vol. 54, pp. 828,836, especially p. 833.
Kim et al., "Curing of Epoxides with O,O-Di-t-butyl Phenylphosphonate as Thermally Latent Initiator," Sep. 29, 2000, J. Applied Polymer Science, vol. 81, pp. 2347-2351, especially p. 2349.
Rao et al., J. Org. Chem., vol. 65, No. 22, 2000, pp. 7323-7344.
U.S. Appl. No. 10/641,412, filed Aug. 15, 2003, Lindsey et al.
Gryko et al.; "Parallel synthesis of *meso*-substituted corroles and *meso*-substituted [22]pentaphyrins(1.1.1.0.0) from diacyldipyrromethanes" *J. Porphyrins Phthalocyanines* 7 239-248 (2003).
Rao et al.; "Rational Syntheses of Porphyrins Bearing up to Four Different Meso Substituents" *J. Org. Chem.* 2000 65, 7323-7344 (2000).

* cited by examiner

*Primary Examiner* — Susannah Chung
(74) *Attorney, Agent, or Firm* — Myers Bigel Sibley & Sajovec, P.A.

(57) ABSTRACT

A method of making a phosphono-substituted dipyrromethane comprises reacting an aldehyde or acetal having at least one phosphono group substituted thereon with pyrrole to produce a phosphono-substituted dipyrromethane; and wherein the phosphono is selected from the group consisting of dialkyl phosphono, diaryl phosphono, and dialkylaryl phosphono. Additional methods, intermediates and products are also described.

4 Claims, No Drawings

SYNTHESIS OF PHOSPHONO-SUBSTITUTED PORPHYRIN COMPOUNDS FOR ATTACHMENT TO METAL OXIDE SURFACES

CROSS-REFERENCE TO RELATED APPLICATIONS

The present application claims priority to and is a divisional of U.S. patent application Ser. No. 12/473,438, filed May 28, 2009, now U.S. Pat. No. 8,080,653 now allowed, which is a divisional of U.S. patent pplication No. 11/937,808, filed Nov. 9, 2007, now issued as U.S. Pat. No. 7,553,977, which is a divisional of U.S. patent application No. 11/553,542, filed Oct. 27, 2006, now issued as U.S. Pat. No. 7,314,941, which is a divisional of U.S. patent application No. 10/698,255, filed Oct. 31, 2003, now issued as U.S. Pat. No. 7,148,361, the disclosures of each of which are incorporated by reference herein in their entirety.

STATEMENT OF GOVERNMENT SUPPORT

This invention was made with Government support under grant number MDA972-01-C-0072 from DARPA. The Government has certain rights to this invention.

FIELD OF THE INVENTION

The present invention concerns methods for the synthesis of porphyrinic compounds, and intermediates thereof, which compounds are useful for attachment to metal oxide surfaces for the production of solar cells and molecular memory devices.

BACKGROUND OF THE INVENTION

We recently described a new design for a molecular-based memory device wherein a layer of redox-active molecules is tethered to an ultra-thin dielectric surface, which in turn is deposited on a semiconductor.[1] The dielectric layer and the molecular tether (linker and surface attachment group) both provide barriers to electron transfer between the semiconductor and the redox-active molecule. In this type of molecular-based field effect transistor, the charge stored in the molecules can change the current level in the transistor, thereby affording a non-destructive means by which the charge state of the molecules can be detected.

In contrast with conventional semiconductor-based devices, the use of charge-storage molecules exploits the power of synthetic design to tailor molecules that operate at low voltage and that provide multiple charged states. Great latitude also exists in the design of the barriers presented by both the tether and the dielectric layer. The barrier presented by the tether can be tuned via synthetic organic chemistry while that of the dielectric can be tuned by semiconductor-processing techniques. In particular, the composition (and length) of the tether can be varied from insulating aliphatic groups to more conducting conjugating species. Likewise, composition of the dielectric layer can be a commonly used $SiO_2$ layer or a metal oxide such as $HfO_2$, $ZrO_2$, etc.

Our preliminary studies employed ferrocenylmethylphosphonic acid as the charge-storage molecule.[1] The phosphonic acid group anchors the charge-storage molecule to the oxide surface. The initial success of this approach has prompted us to investigate the synthesis of a much wider variety of charge-storage molecules, particularly porphyrinic molecules, which bear phosphonic acid-terminated linkers. Porphyrins bearing phosphonic acid tethers have been synthesized and attached to oxide surfaces for a variety of other applications including solar energy, oxidative catalysis, sensing, and recognition of polysaccharides.[2-14]

The synthetic approaches that have been employed to prepare porphyrins bearing phosphonic acid/phosphonate units can be characterized by (1) whether the phosphonate unit is introduced into precursors to the porphyrin or by derivatization of a preexisting porphyrin, (2) whether statistical or rational routes are employed, (3) the number and pattern of phosphonate groups at the perimeter of the porphyrin, (4) the type of phosphonic acid protecting group employed, (5) the nature of the central metal, and (6) the method of cleavage of the phosphonate protecting groups.

$A_4$-Porphyrins bearing four arylphosphonic acids have been prepared by condensation of a dialkoxyphosphorylbenzaldehyde with pyrrole followed by deprotection of the free base porphyrin.[2] Alternatively, the free base porphyrin can be metalated followed by deprotection.[4,5] $A_4$-porphyrins bearing four alkylphosphonic acids have been prepared by derivatization of a reactive halo-substituted porphyrin.[5-7] $A_3B$-porphyrins bearing a single phosphonic acid have been prepared by a mixed-aldehyde condensation of a dialkoxyphosphorylbenzaldehyde, benzaldehyde, and pyrrole;[4] or by derivatization of a porphyrin bearing a single reactive halo group.[6,14] Trans-$A_2B_2$-porphyrins bearing two phosphonic acid groups have been prepared by condensation of a dialkoxyphosphorylbenzaldehyde and dipyrromethane.[12] Chlorins bearing two phosphonic acids have been prepared by derivatization of a deuterochlorin-dibromide with tris(trimethylsilyl)phosphite.[9] In each case, the porphyrinic species were employed as the free base or as a metal chelate that is rather robust toward the acidic conditions for cleavage of the dialkyl phosphonate. The metals include Mn,[4,5] Fe,[9] Co,[9] Ni,[9] Pd,[6] and Os,[7] which are all categorized in the porphyrin field as class I or class II metals, affording chelates that are exceptionally resilient toward acids.[15] In general, phosphonic acids combine with metals to give extended, often insoluble, metal phosphonates. A rare case wherein metalation was performed in the presence of a free phosphonic acid employed a porphyrin superstructure containing a hindered phosphonic acid.[14]

One of the considerable attractions of molecular information storage is the ability to tune the properties of the charge-storage molecules through molecular design. In studies of thiol-derivatized porphyrins, we found that the period during which the oxidized molecules remained charged (i.e., the charge-retention time) depends quite sensitively on the length of the tether (linker and surface attachment group). For example, as the number of methylene groups in the tether phenyl-$(CH_2)_n$—S— increased along the series 0, 1, 2, and 3, the charge-retention time increased from 116, 167, 656 to 885 s. The rate of electron-transfer (reading process) also slowed with increase of linker length. Moreover, the quality (uniformity, integrity) of the self-assembled monolayers (SAMs) increased in going from the phenylthio tether (n=0) to the phenylalkylthio tethers (n=1-3).[16]

SUMMARY OF THE INVENTION

A first aspect of the invention is a method of making a phosphono-substituted dipyrromethane, comprising: reacting an aldehyde or acetal having at least one phosphono group substituted thereon with pyrrole to produce a phosphono-substituted dipyrromethane; and wherein the phosphono is selected from the group consisting of dialkyl phosphono, diaryl phosphono, and dialkylaryl phosphono. In some embodiments the aldehyde or acetal is coupled to the at least one phosphono by a linking group (e.g., aryl, alkyl, alkylaryl, and alkylarylalkyl linking groups). In some embodiments the aldehyde or acetal has three phosphono groups substituted thereon.

A second aspect of the present invention is a method of making a phosphono substituted dipyrromethane, comprising: reacting a halo-substituted dipyrromethane with a phosphite to produce a phosphono-substituted dipyrromethane. The phosphite is generally a dialkyl phosphite, diaryl phosphite, or dialkylaryl phosphite, and the phosphono is generally a dialkyl phosphono, diaryl phosphono, or dialkylaryl phosphono.

In some embodiments, the halo is coupled to the dipyrromethane by a linking group such as described above.

A third aspect of the present invention is a 5-phosphono-dipyrromethane, wherein the phosphono is selected from the group consisting of dialkyl phosphono, diaryl phosphono, and dialkylaryl phosphono. In some embodiments the phosphono is coupled to the dipyrromethane by a linking group such as described above.

A fourth aspect of the present invention is a method of making a 5-phosphono, 1-acyldipyrromethane, comprising: reacting a 5-phosphonodipyrromethane with a Grignard reagent to produce an intermediate compound; and then reacting the intermediate compound with a Mukaiyama reagent to produce a 5-phosphono, 1-acyldipyrromethane. In some embodiments the 5-phosphono is selected from the group consisting of dialkyl phosphono, diaryl phosphono, and dialkylaryl phosphono and in some embodiments the phosphono is coupled to the dipyrromethane by a linking group such as described herein.

A fifth aspect of the present invention is a dipyrromethane selected from the group consisting of (a) 1-phosphonoacyl-dipyrromethanes, and (b) 5-phosphono, 1-acyldipyrromethanes. In some embodiments the 5-phosphono is dialkyl phosphono, diaryl phosphono, or dialkylaryl phosphono. Where the compound is a 5-phosphono, 1-acyldipyrromethane, the 1-acyl group may be a 1-phosphonoacyl group to provide a compound having two phosphono groups thereon.

A sixth aspect of the present invention is a method of making a 9-halo, 5-phosphono, 1-acyldipyrromethane, comprising: halogenating a 5-phosphono, 1-acyldipyrromethane to produce a 9-halo, 5-phosphono, 1-acyldipyrromethan; wherein the phosphono is selected from the group consisting of dialkyl phosphono, diaryl phosphono, and dialkylaryl phosphono. The phosphono may be coupled to the dipyrromethane by a linking group such as described herein.

A seventh aspect of the invention is a 9-halo, 5-phosphono, 1-acyldipyrromethane compound. The phosphono is preferably dialkyl phosphono, diaryl phosphono, or dialkylaryl phosphono. The phosphono may be coupled to the dipyrromethane by a linking group such as described herein.

An eighth aspect of the invention is a method of making a chlorin, comprising: reducing a 9-halo, 5-phosphono, 1-acyl-dipyrromethane to produce a first reaction product; and then reacting the first reaction product with a western half to produce the chlorin; wherein the phosphono is selected from the group consisting of dialkyl phosphono, diaryl phosphono, and dialkylaryl phosphono. The phosphono may be coupled to the dipyrromethane by a linking group such as described herein.

A ninth aspect of the present invention is a chlorin having a phosphono group coupled thereto at the 5 position, the 10 position, or both the 5 and 10 position. In some embodiments the phosphono may be dialkyl phosphono, diaryl phosphono, or dialkylaryl phosphono, and the phosphono may be coupled to the chlorin by a linking group such as described herein.

A tenth aspect of the invention is a method of making a porphyrin substituted at the 5 position with at least one phosphono group, comprising: reacting a 5-phosphono-substituted dipyrromethane with a dipyrromethane-dicarbinol to produce the porphyrin; wherein the phosphono is selected from the group consisting of dialkyl phosphono, diaryl phosphono, and dialkylaryl phosphono. In some embodiments the phosphono is coupled to the dipyrromethane by a linking group such as described herein. In some embodiments the at least one phosphono group consists of three phosphono groups.

An eleventh aspect of the invention is a porphyrin substituted at both the 5 position and the 10 position with a phosphono group, such as described herein.

A twelfth aspect of the invention is a method of making a substituted porphyrin compound, comprising: reacting a halo-substituted porphyrin with a phosphite or a salt thereof to produce a porphyrin having a phosphono group coupled thereto; wherein the phosphite is selected from the group consisting of dialkyl phosphite, diaryl phosphite, dialkylaryl phosphite, trialkyl phosphite, triaryl phosphite, and trialkylaryl phosphite; and wherein the phosphono is selected from the group consisting of dialkyl phosphono, diaryl phosphono, and dialkylaryl phosphono. In some embodiments the halo-substituted porphyrin comprises a porphyrin having a halo group coupled thereto by an intermediate linking group such as described herein. The method may further comprise the step of metalating the porphyrin having a phosphono group coupled thereto.

A thirteenth aspect of the invention is a method of making a phosphono-substituted porphyrin or chlorin, comprising: reacting a porphyrin or chlorin having a protected phosphono group substituted thereon at the 5 position with a trialkysily halide and a base in a solvent to produce a porphyrin or chlorin having a phosphonic acid group substituted thereon. In some embodiments the phosphono is coupled to the porphyrin or chlorin with an intermediate linking group such as described herein.

A fourteenth aspect of the invention is a method of making coupled porphyrins, comprising: reacting (i) a first porphyrin substituted with a halo or ethyne group and a protected phosphono group with (ii) a second porphyrin having an ethyne or halo group in a Sonogashira reaction to couple the first and second porphyrins; wherein the first porphyrin is substituted with halo when the second porphyrin is substituted with ethyne, and the first porphyrin is substituted with ethyne when the second porphyrin is substituted with halo.

The foregoing and other objects and aspects of the present invention are explained in greater detail in the specification set forth below.

DETAILED DESCRIPTION OF THE PREFERRED EMBODIMENTS

"Alkyl," as used herein, refers to a straight or branched chain hydrocarbon, for example containing from 1 to 10 or 20 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like. When used as a linking group alkyl as described herein includes two covalent bonds, one to each linked group.

"Aryl," as used herein, refers to a monocyclic carbocyclic ring system or a bicyclic carbocyclic fused ring system having one or more aromatic rings. Representative examples of aryl include azulenyl, indanyl, indenyl, naphthyl, phenyl, tetrahydronaphthyl, and the like. When used as a linking group alkyl as described herein includes two covalent bonds, one to each linked group.

"Phosphono" as used herein refers to unprotected phosphono groups of the formula —R—P(=O)(OH)$_2$, where R is a linking group or a covalent linkage, as well as protected phosphono groups of the formula —R—P(=O)(OR$^1$)$_2$, where R is a linking group or a covalent bond and R$^1$ is alkyl, aryl, or alkylaryl.

"Acyl" as used herein means a —C(=O)R group, where R is a suitable substituent such as alkyl, aryl, or alkylaryl, which substituent may be substituted or unsubstituted.

"Phosphonoacyl" as used herein means a group of the formula —C(=O)R, where R is a phosphono group as described above.

"Dialkylaryl phosphono" as used herein refers to a compound of the formula —P(=O)(OR$^1$R$^2$)$_2$ where R$^1$ is alkyl and R$^2$ is aryl. Likewise "trialkylaryl" refers to the presence of three substitutents of the formula —R$^1$R$^2$ on the indicated group (where R$^1$ is alkyl and R$^2$ is aryl).

"Halo" as used herein refers to halogens such as chloro, bromo or iodo.

"Linking group" as used herein refers to any suitable group having two covalent bonds, one to each linked group, such as alkyl, aryl, alkylaryl, or alkylarylalkyl linking groups. Additional covalent bonds are included when additional groups are linked.

"Porphyrin" as used herein refers to substituted or unsubstituted porphyrins and includes porphyrins with extra rings ortho-fused, or ortho-perifused, to the porphyrin nucleus, porphyrins having a replacement of one or more carbon atoms of the porphyrin ring by an atom of another element (skeletal replacement), derivatives having a replacement of a nitrogen atom of the porphyrin ring by an atom of another element (skeletal replacement of nitrogen), derivatives having substituents other than hydrogen located at the peripheral (meso-, beta-) or core atoms of the porphyrin, porphyrins with saturation of one or more bonds of the porphyrin (hydroporphyrins, e.g., chlorins, bacteriochlorins, isobacteriochlorins, decahydroporphyrins, corphins, pyrrocorphins, etc.), porphyrins obtained by coordination of one or more metals to one or more porphyrin atoms (metalloporphyrins), porphyrins having one or more atoms, including pyrrolic and pyrromethenyl units, inserted in the porphyrin ring (expanded porphyrins), porphyrins having one or more groups removed from the porphyrin ring (contracted porphyrins, e.g., corrin, corrole) and combinations of the foregoing derivatives (e.g. phthalocyanines, subphthalocyanines, and porphyrin isomers). Preferred porphyrins comprise at least one 5-membered ring and more preferably include four 5-membered rings, each of which includes a hetero atom such as N, S, or O, preferably N in a position for formation of a coordination bond.

"Grignard reagent" and "Mukaiyama reagent" are as described in further detail below.

"Eastern half" and "Western half" are as described in further detail below.

The disclosures of all United States patent references cited herein are to be incorporated by reference herein in their entirety.

The present invention provides methods of making a phosphono-substituted dipyrromethane. In general, such methods comprise reacting an aldehyde or acetal having at least one phosphono group substituted thereon with pyrrole to produce a phosphono-substituted dipyrromethane, with the dipyrromethane preferably substituted by the phosphono group at the 5 position thereof (see for example Scheme 4 below). In general, the phosphono group may be a dialkyl phosphono, diaryl phosphono, or dialkylaryl phosphono group. The aldehyde or acetal may be coupled to the at least one dialkyl phosphono by a linking group. In some embodiments, the aldehyde or acetal has three phosphono groups substituted thereon (e.g., by coupling to dipyrromethane at the 5 position a group of the formula —R$^1$(R$^2$Z)$_3$, where R$^1$ is a first linking group, R$^2$ is a second linking group, and Z is a phosphono group). Such reactions are generally carried out with an acid catalyst, or without an acid catalyst in the presence of heat. Depending upon whether or not a catalyst is used, the reactions are carried out at an elevated temperature of up to about 100° C., and more typically at a temperature of 50 to 100° C. Any suitable acid catalyst may be used, including indium trichloride, scandium triflate, TFA, BF$_3$ etherate, etc. While the pyrrole serves as the solvent a cosolvent or diluent may optionally be included, examples of which include but are not limited to toluene, methylene chloride, chloroform, etc.

Another method of making a phosphono substituted dipyrromethane described herein comprises reacting a halo-substituted dipyrromethane with a phosphite to produce a phosphono-substituted dipyrromethane (see for example Scheme 4 below). In general, the phosphite is a dialkyl phosphite, a diaryl phosphite, or a dialkylaryl phosphite, and the corresponding phosphono is a dialkyl phosphono, a diaryl phosphono, or a dialkylaryl phosphono. The halo is preferably coupled to the dipyyromethane at the 5 position, and may be coupled to the dipyrromethane by a linking group. Where the linking group is or includes an aryl to which the halo is coupled, the halo may be coupled to the aryl at the ortho, meta or para position. In general, such reactions are catalyzed with a metal such as palladium or nickel and are carried out in a suitable solvent such as toluene or triethylamine, and are carried out at any suitable temperature such as 50 to 150° C. (e.g., under reflux) for any suitable time, such as 1-24 hours (e.g., overnight). An alternative, when the dipyrromethane is substituted with a haloalkyl, is to treat the dipyrromethane with a trialkylphosphite or triarylphosphite at a temperature of 0 or 50 to 150° C. (salts can be reacted at room temperature).

The present invention further provides a method of making a 5-phosphono, 1-acyldipyrromethane. In general, the method comprises reacting a 5-phosphonodipyrromethane with a Grignard reagent to produce an intermediate compound, and then reacting the intermediate compound with a Mukaiyama reagent to produce a 5-phosphono, 1-acyldipyrromethane (see for example Scheme 6 herein). The 5-phosphonodipyrromethane can be as described herein and produced by methods such as described above. The reaction can be carried out in accordance with techniques known to those skilled in the art (see, e.g., U.S. Pat. Nos. 6,617,282, 6,608,212, 6,603,000 and 6,600,040, describing Grignard reagents).

Alternatively, the phosphono group can be introduced at the 1-position of the dipyrromethane in an acylation reaction between a dipyrromethane and a Mukaiyama reagent bearing the phosphono functional group. The Mukaiyama reagent is, in general, any suitable Mukaiyama reagent, typically a 2-S-pyridyl phosphono thioate, where phosphono may be protected or unprotected as described herein and may include a linking group as described herein. The reaction may be carried out in any suitable solvent, such as an ethereal solvent such as THF, and is preferably carried out under chilled conditions. In this manner, monoacyl dipyrromethanes bearing a phosphono group at the 1-, 5-, or 1- and 5-positions of the dipyrromethane can be prepared, by inclusion of the phosphono group on the acyl group.

A method of making a 9-halo, 5-phosphono, 1-acyldipyrromethane is also described herein. The method comprises halogenating a 5-phosphono, 1-acyldipyrromethane to produce a 9-halo, 5-phosphono, 1-acyldipyrromethane (see for example Scheme 8 below). In general, the phosphono group may be a dialkyl phosphono, diaryl phosphono, or dialkylaryl phosphono group (which may be coupled to the 5 position by a linking group as described above), and the halo may be chloro, bromo or iodo, preferably bromo. Any halogenating agent may be used, including but not limited to N-chlorosuccinimide, N-bromosuccinimide, N-iodosuccinimide, 1,3-dichloro-5,5-dimethylhydantoin, 1,3-dibromo-5,5-dimethylhydantoin, chlorine, bromine, and iodine. The reaction is preferably carried out at a temperature less than room temperature, most preferably 0 to −100° C., in any suitable solvent such as tetrahydrofuran, dioxane, diethyl ether or other ethereal solvents, but preferably THF.

A method of making a chlorin is also described herein. The method comprises reducing a 9-halo, 5-phosphono, 1-acyldipyrromethane to produce a first reaction product (an "Eastern half"); and then reacting the first reaction product eastern half with a Western half to produce the chlorin (see for example Scheme 8 below). The 9-halo, 5-phosphono, 1-acyldipyrromethane may be produced as described above, and in general, the phosphono may be dialkyl phosphono, diaryl phosphono, or dialkylaryl phosphono. The terms "Eastern half" and "Western half" are known in the art of chlorin chemistry; reactions for producing a chlorin from eastern and western halves are known in the art of chlorin chemistry, and can be carried out in accordance with known techniques or variations thereof which will be apparent to those skilled in the art given the present disclosure. See, e.g., U.S. Pat. No. 6,559,374 to Lindsey and Balasubramanian.

A method of making a porphyrin substituted at the 5 position with at least one phosphono group is also described herein. The method comprises reacting a 5-phosphono-substituted dipyrromethane with a dipyrromethane-dicarbinol to produce the porphyrin (see for example Scheme 5 below). In general, the phosphono may be a dialkyl phosphono, diaryl phosphono, or dialkylaryl phosphono, and in general the phosphono may be coupled to the dipyrromethane by a linking group as described above. In some embodiments the at least one phosphono group consists of three phosphono groups (e.g., by coupling to the dipyrromethane at the 5 position a group of the formula —$R^1(R^2Z)_3$, where $R^1$ is a first linking group, $R^2$ is a second linking group, and Z is a phosphono group). The methods may be carried out in accordance with known techniques, such as described in US Patent Application No. 2003/0096978 A1 (published May 22, 2003) to Lindsey, Geier and Yu. In general, the reactions may be carried out at any suitable temperature and pressure, such as room temperature and ambient pressure. In general the reactions are carried out within a time of 1 to 2 hours. Solvents which may be used to carry out the present invention preferably have a dielectric constant of about 20, 15, or 10 or less, at room temperature (i.e., 25° C.). The solvent may be a single compound or mixtures thereof. Preferably the solvent is non-aqueous. Particular examples of suitable solvents include, but are not limited to, chlorinated aliphatic hydrocarbons (e.g., dichloromethane, chloroform, 1,2-dichloroethane, 1,1,1-trichloroethane, 1,1,2,2-tetrachloroethane, 1,1-dichloroethylene, cis-1,2-dichloroethylene, trans-1,2-dichloroethylene, trichloroethylene, etc.); chlorinated aromatic hydrocarbons (e.g., chlorobenzene, 1,2-dichlorobenzene, 1,3-dichlorobenzene, 1,4-dichlorobenzene, 1-chloronaphthalene, etc.); hydrocarbons (e.g., benzene, toluene, xylene, ethylbenzene, mesitylene, durene, naphthalene); ethers (e.g., ethyl ether, propyl ether, tetrahydrofuran, p-dioxane, anisole, phenyl ether, etc.); esters (e.g., ethyl acetate, methyl acetate, ethyl benzoate, butyl phthalate, etc.); glymes (e.g., 2-methoxyethanol, 2-butoxyethanol), and other solvents such as carbon disulfide, tributyl borate, etc., and mixtures of the foregoing. Any suitable electron-pair acceptor may be used as the Lewis acid catalyst in the present invention, including, but not limited to, $CsCl$, $SmCl_3 \cdot 6H_2O$, $InCl_3$, $CrF_3$, $AlF_3$, $Sc(OTf)_3$, $TiF_4$, $BEt_3$, $GeI_4$, $EuCl_3 \cdot nH_2O$, $LaCl_3$, $Ln(OTf)_3$ where Ln=a lanthanide, etc. The concentration of the Lewis acid may range, for example, from 0.001 or 0.01 mmol/L to 100 or 500 mmol/L, or more.

The preparation of a porphyrin bearing two dialkyl phosphono diaryl phosphono, or dialkylaryl phosphono groups at the 5- and 10-positions (cis-$A_2B_2$ or cis-$A_2BC$ type porphyrins) can be prepared by condensation of a dipyrromethane-dicarbinol bearing two dialkyl phosphono, diaryl phosphono, or dialkylaryl phosphono groups at the 1- and 5-positions with a dipyrromethane.

Reactions of Porphyrins. The present invention also provides for reactions of porphyrins. Among other things the present invention provides a method of making a substituted porphyrin compound, comprising: reacting a halo-substituted porphyrin with a phosphite, or a salt thereof, to produce a porphyrin having a phosphono group coupled thereto (see for example Scheme 11). In general the phosphite may be a dialkyl phosphite, diaryl phosphite, dialkylaryl phosphite, trialkyl phosphite, triaryl phosphite, or trialkylaryl phosphite, and the corresponding phosphono may be a dialkyl phosphono, diaryl phosphono, or dialkylaryl phosphono. The halo group may be coupled to the porphyrin by an intermediate linking group as described above. In some embodiments, the porphyrin on which the reaction is performed may be a member of a double-decker or triple-decker sandwich coordination compound. Reactions may be carried out in the same manner as described in connection with phosphites above, and may further comprise the step of metalating the porphyrin in accordance with known techniques.

A method of making a phosphonic acid-substituted porphyrin or chlorin is also described herein. The method generally comprises reacting a porphyrin or chlorin having a protected phosphono group substituted thereon at the 5 position with a trialkyl silylhalide and a base in a solvent to produce a porphyrin or chlorin having a phosphonic acid group substituted thereon (see for example Scheme 10 below). The phosphono may be coupled to the porphyrin or chlorin with an intermediate linking group such as described above. When porphyrins are used, the porphyrin may be a member of a double-decker or triple-decker sandwich coordination compound. Any suitable trialkylsilyl halide may be used, including but not limited to trimethylsilyl chloride and trimethylsilyl bromide. The base is preferably a tertiary amine, more preferably a trialkylamine and most preferably triethylamine. The reaction may be carried out in any suitable solvent such as $CH_2Cl_2$, $CHCl_3$, chlorobenzene, etc. at any suitable temperature (e.g., 0 to 200° C.) for any suitable time (e.g., 1 to 24 hours) and may conveniently be carried out under reflux in $CHCl_3$.

The present invention further provides a method of making coupled porphyrins, comprising: reacting (i) a first porphyrin substituted with a halo or ethyne group and a protected phosphono group with (ii) a second porphyrin having an ethyne or halo group in a Sonogashira reaction to couple said first and second porphyrins, wherein said first porphyrin is substituted with halo when said second porphyrin is substituted with ethyne, and said first porphyrin is substituted with ethyne when said second porphyrin is substituted with halo (see for example Scheme 9 below). As previously, in some embodiments one or both of the first and second porphyrins may comprise a member of a double-decker or triple-decker sandwich coordination compound. Such reactions may be carried out in accordance with known techniques, including but not limited to those described in U.S. Pat. No. 6,603,070 to Lindsey and Loewe.

Compounds of the present invention (including the products of the processes described herein) are useful, among other things, for the production of polymers thereof which may be immobilized or coupled to a substrate and used as light harvesting rods, light harvesting arrays, and solar cells, as described for example in U.S. Pat. No. 6,407,330 to Lindsey et al. or U.S. Pat. No. 6,420,648 to Lindsey. Compounds of the present invention are also useful immobilized to a substrate for making charge storage molecules and information storage devices containing the same. Such charge storage molecules and information storage devices are known and described in, for example, U.S. Pat. Nos. 6,208,553 to Gryko et al.; 6,381,169 to Bocian et al.; and 6,324,091 to Gryko et al. The compounds of the invention, particularly porphyrins, and including products and intermediates, may comprise a member of a double-decker or triple-decker sandwich coordination compound, such as for use as an information storage molecule, such as described in U.S. Pat. No. 6,212,093 to Li et al. or U.S. Pat. No. 6,451,942 to Li et al.

The present invention is explained in greater detail in the non-limiting Examples set forth below.

Experimental

Example I below shows that synthetic molecules bearing phosphonic acid groups can be readily attached to oxide surfaces. As part of a program in molecular-based information storage, we have developed routes for the synthesis of diverse porphyrinic compounds bearing phenylphosphonic acid tethers. The routes enable (1) incorporation of masked phosphonic acid groups in precursors for use in the rational synthesis of porphyrinic compounds, and (2) derivatization of porphyrins with masked phosphonic acid groups. The precursors include dipyrromethanes, acyldipyrromethanes, and diacyldipyrromethanes. The tert-butyl group has been used to mask the dihydroxyphosphoryl substituent. The di-tert-butyloxyphosphoryl unit is stable to the range of conditions employed in syntheses of porphyrins and multiporphyrin arrays, yet can be deprotected under mild conditions (TMS—Cl/TEA or TMS—Br/TEA in refluxing $CHCl_3$) that do not cause demetalation of zinc porphyrins (class III) or magnesium porphyrins (class IV). The porphyrinic compounds that have been prepared include (1) $A_3B$-, trans-$AB_2C$—, and ABCD-porphyrins that bear a single phenylphosphonic acid group, (2) a trans-$A_2B_2$-porphyrin bearing two phenylphosphonic acid groups, (3) a chlorin that bears a single phenylphosphonic acid group, and (4) a porphyrin dyad bearing a single phenylphosphonic acid group.

In Example II below we describe the synthesis of porphyrins bearing benzylphosphonic acid, hexylphosphonic acid, and tripodal phosphonic acid tethers. The benzyl and hexyl linkers are longer than a phenyl unit while the tripodal tether anchors the redox-active molecule in a 3-point contact and enforces a vertical orientation of the charge-storage molecule. The key design issues for tripods are (1) the nature of the atom or molecular unit to which the three legs of the tripod are attached, (2) the composition and length of the tripod legs, and (3) the nature of the three terminal groups for surface attachment. Diverse tripodal tethers have been prepared for attaching molecules to surfaces. Tripods containing a C atom,[17-30] a Si atom,[31] or an adamantane[26,32-35] unit at the central core of the tripod have been prepared. The tripod legs include methyl[22,34] ethyl,[21] propyl,[17,19,20,22,23] alkyl ether,[18] phenyl,[26,32,33] benzyl,[24,25,27,30] biphenyl,[28,29] diphenylethyne,[31,35] and oligoethynylphenyl[35] structures. The terminal groups include thiol,[17,19,20,22,24,25,27,30,34] S-acetylthio,[23,25,27,31,35] thiocyanate,[22] alcohol,[22,34] ester,[18,26,32,33,34] carboxylic acid,[18,21,26,33] diethyl phosphonate,[28] or phosphonic acid[28,29] groups. Some of the tripods bear redox-active groups including ferrocene,[21,22] viologen,[28,29] fullerene,[18,25,27] ruthenium-tris(bpy),[26,32] or oligothiophene[25,27,30] units. Dendrimeric tripods bearing more than three sites of attachment also have been prepared.[17,18,21,36]

A tripod built around a tetraarylmethane structure containing three terminal phosphonic acid groups appeared most attractive for our purposes owing to the rigid, compact, and tetrahedral architecture. The tripods of this type that have been prepared incorporate methylthiol[24,25,27,30] or ester[26,32] termini attached to phenyl legs, or dialkyl phosphono termini attached to biphenyl legs.[28,29] The synthesis of the thiol-terminated tetraarylmethane tripod proceeded through the valuable intermediate 1,1,1-tris(4-bromomethylphenyl)(4-bromophenyl)methane.[27] We felt that the route for preparing this intermediate could be adapted to incorporate porphyrins and benzylphosphonic acid groups.

Example I

1. Approach. A variety of protecting groups have been used for phosphonic acids, including methyl, ethyl, allyl, and tert-butyl groups.[2-14,37-43] For our application, a key issue concerns the stability of the metalloporphyrin towards conditions employed for protecting group removal, as inadvertent demetalation of the porphyrin would complicate the synthesis of mixed-metal multiporphyrin arrays. Accordingly, the ideal masking agent should meet the following requirements: (1) Compatibility with porphyrin forming conditions, including acid catalysis and DDQ oxidation conditions. (2) Stability towards a variety of metalation conditions. (3) Compatibility with Pd-mediated coupling reactions. (4) Undergo cleavage without demetalation of the metalloporphyrins.

Mild conditions for the cleavage of a dialkyl phosphonate to give the phosphonic acid originate with Rabinowitz, who first used trimethylsilyl chloride (TMS—Cl) followed by hydrolysis of the resulting bis(trimethylsilyl) phosphonate.[44] Modifications of this approach have led to the following conditions: (1) TMS—Br (neat);[37] (2) TMS—Br/$CH_3CN$[42] or $CH_2Cl_2$;[40] (3) TMS—Cl/TEA;[45] and (4) TMS—Br/TEA/$CH_2Cl_2$.[41] Some of these approaches have been applied to the cleavage of a diethyl porphyrin-phosphonate: (1) TMS—Br/$CH_2Cl_2$ (free base porphyrins);6,7,12 (2) TMS—Br/TEA/DMF (Mn-porphyrin);[13] and (3) NaBr/TMS—Cl/TEA/DMF (Mn-porphyrin).[4]

We have examined methods for the introduction and cleavage of various phosphonic acid protecting groups that are compatible with the preparation of diverse porphyrinic compounds. Several possible masking agents [2-trimethylsilylethyl, 2-cyanoethyl, 2-chloroethyl, methyl] were examined but found inapplicable for the preparation of porphyrin-phosphonic acids. The tert-butyl group has been used for the protection of phosphates in nucleotide syntheses with facile removal under mild non-acidic conditions (TMS—Cl/TEA).[45] We therefore employed the tert-butyl group as masking agent in the work described herein.

2. Synthesis. A sample of 4-bromobenzaldehyde dimethylacetal[46] was coupled with di-tert-butylphosphite to give 4-(di-tert-butyloxyphosphoryl)benzaldehyde dimethylacetal. The latter was used in a mixed-aldehyde condensation[47] with pyrrole under standard conditions of $BF_3 \cdot O(Et)_2$-ethanol cocatalysis[48] followed by oxidation with DDQ to give porphyrin 1. Porphyrin 1 was metalated with $Zn(OAc)_2 \cdot 2H_2O$ in $CHCl_3$/methanol to afford zinc porphyrin Zn1 in 73% yield (Scheme 1). Cleavage of the tert-butyl groups was achieved by following the known procedure[45] with TMS—Cl/TEA in refluxing $CHCl_3$ (stabilized with amylenes). In this manner, the porphyrin Zn2 was obtained without demetalation in 89% yield. Note that $CHCl_3$ stabilized with amylenes rather than ethanol was used to avoid the possible reaction of ethanol with TMS—Cl.

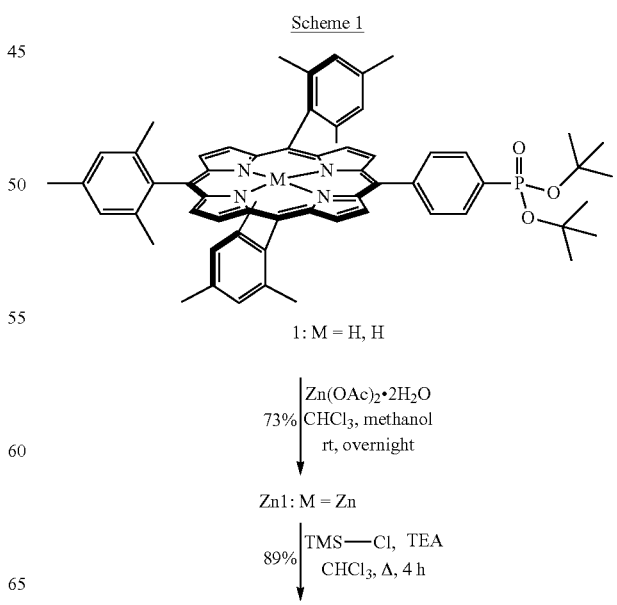

Scheme 1

1: M = H, H

73% | $Zn(OAc)_2 \cdot 2H_2O$
      $CHCl_3$, methanol
      rt, overnight

Zn1: M = Zn

89% | TMS—Cl, TEA
      $CHCl_3$, Δ, 4 h

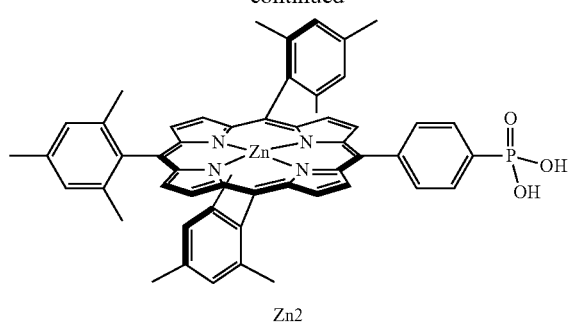

Zn2

The synthesis of magnesium porphyrin Mg1 was first tried using the heterogeneous magnesium insertion procedure.[49] Porphyrin 1 was treated with $MgI_2$ and DIEA in $CH_2Cl_2$ at room temperature, but these conditions resulted in cleavage of the tert-butyl groups. However, magnesium insertion using the homogeneous procedure[50] (ethereal $MgI_2$-DIEA reagent in $CH_2Cl_2$) gave Mg1 in 71% yield. Treatment of Mg1 with TMS—Cl/TEA in refluxing $CHCl_3$ or THF did not cause cleavage of the tert-butyl groups. However, use of TMS—Br/TEA in refluxing $CHCl_3$ gave porphyrin-phosphonic acid Mg2 in 77% yield (Scheme 2).

Scheme 2

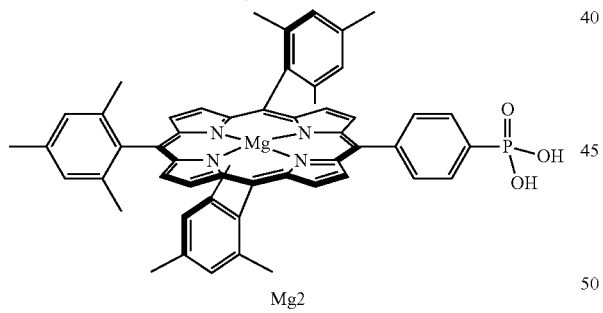

We also examined the diethyl phosphono porphyrin Zn3, which was prepared from 4-(diethoxyphosphoryl)benzaldehyde[4] in the same manner as for Zn1. We found that Zn3 could be deprotected in 81% yield without affecting the metalation state by using the TMS—Br/TEA reagent in refluxing $CHCl_3$. On the other hand, treatment of Zn3 with TMS—Br in the absence of TEA (employed for the deprotection of diethyl phosphonates)[6] at room temperature caused demetalation in addition to cleavage of the ethyl groups, affording the free base porphyrin-phosphonic acid 2 in 79% yield (Scheme 3). Porphyrin 2 was metalated with $Zn(OAc)_2 \cdot 2H_2O$ under standard conditions, giving Zn2 in 77% yield. The successful metalation of a porphyrin bearing a free phosphonic acid was surprising and may stem in part from the suppression of aggregation afforded by the three mesityl groups.

Scheme 3

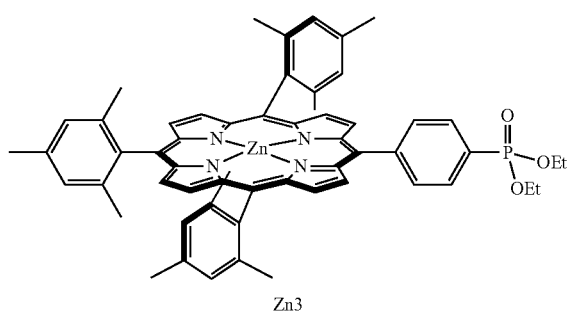

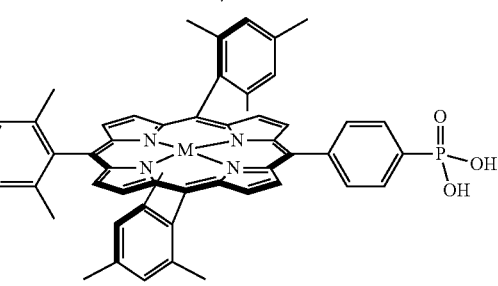

The success of the above studies prompted us to employ the di-tert-butyl phosphono group in a variety of porphyrin precursors. Accordingly, reaction of acetal 4 with excess pyrrole following a standard procedure[51] afforded dipyrromethane 6 in 31% yield (Scheme 4). Alternatively, Pd-mediated coupling of 5-(4-bromophenyl)dipyrromethane (5)[51] with di-tert-butylphosphite gave 6 in 43% yield. Dipyrromethane 6 is a valuable synthon for use in porphyrin chemistry.

Scheme 4

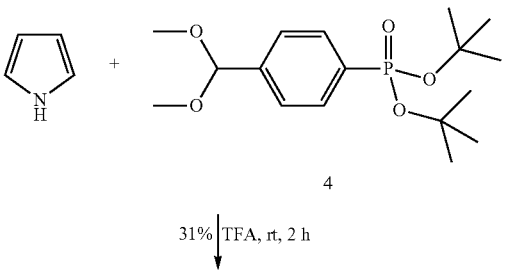

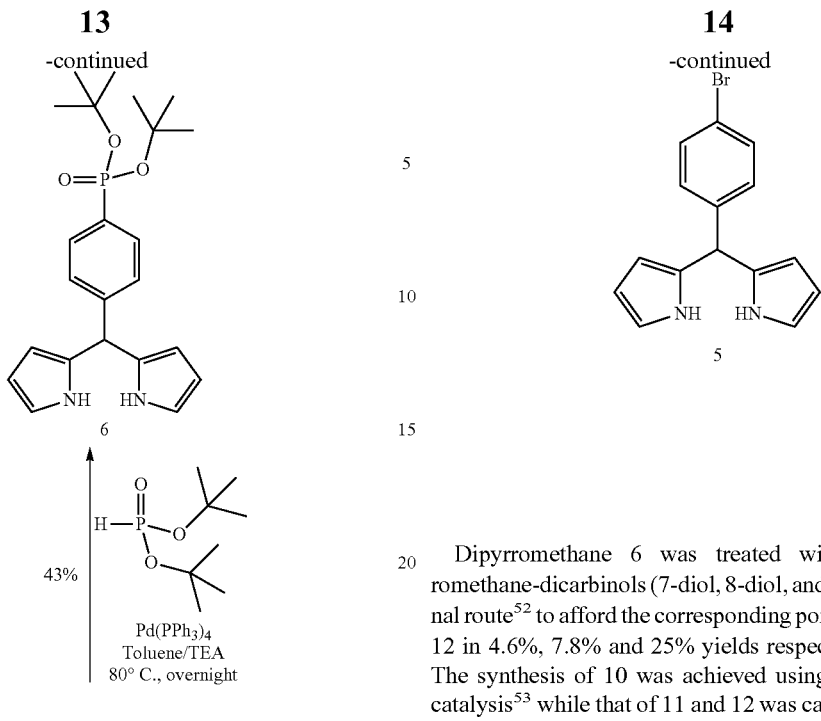
Dipyrromethane 6 was treated with various dipyrromethane-dicarbinols (7-diol, 8-diol, and 9-diol)[52] in a rational route[52] to afford the corresponding porphyrins 10, 11, and 12 in 4.6%, 7.8% and 25% yields respectively (Scheme 5). The synthesis of 10 was achieved using $Yb(OTf)_3$ as acid catalysis[53] while that of 11 and 12 was carried out with TFA.
Scheme 5
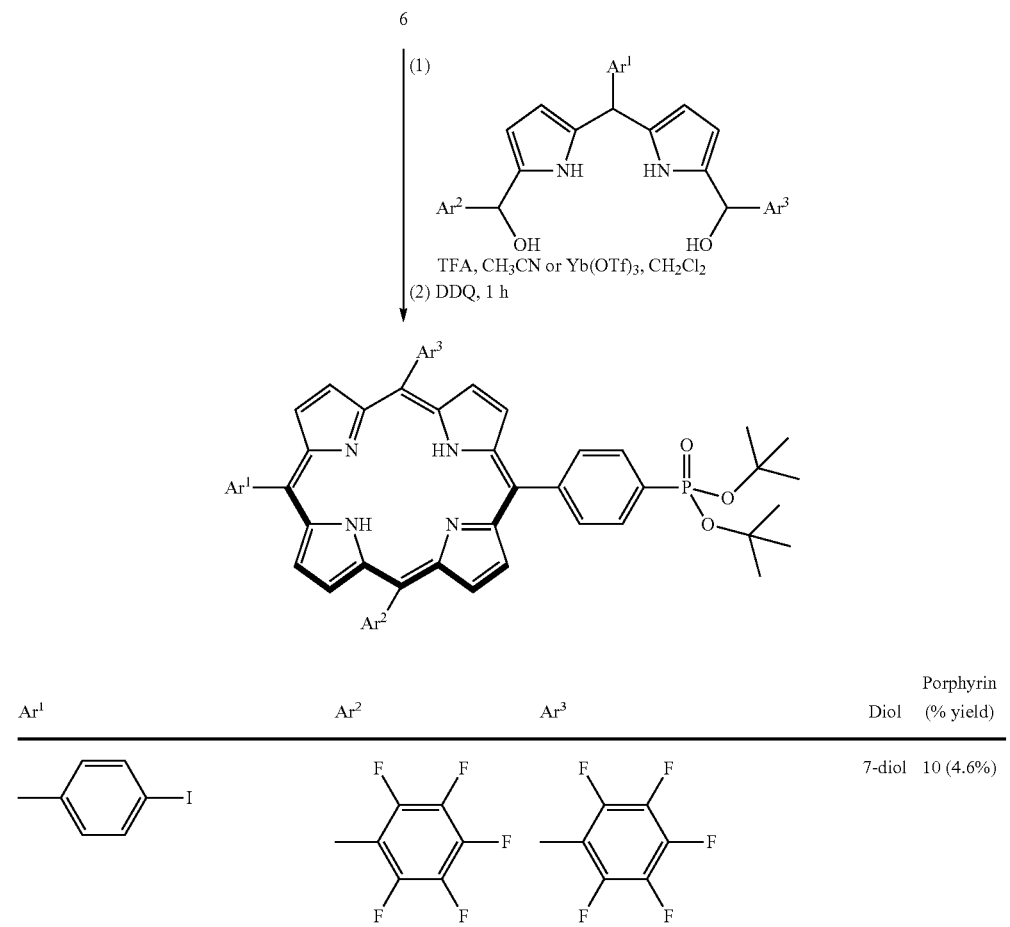

Scheme 5

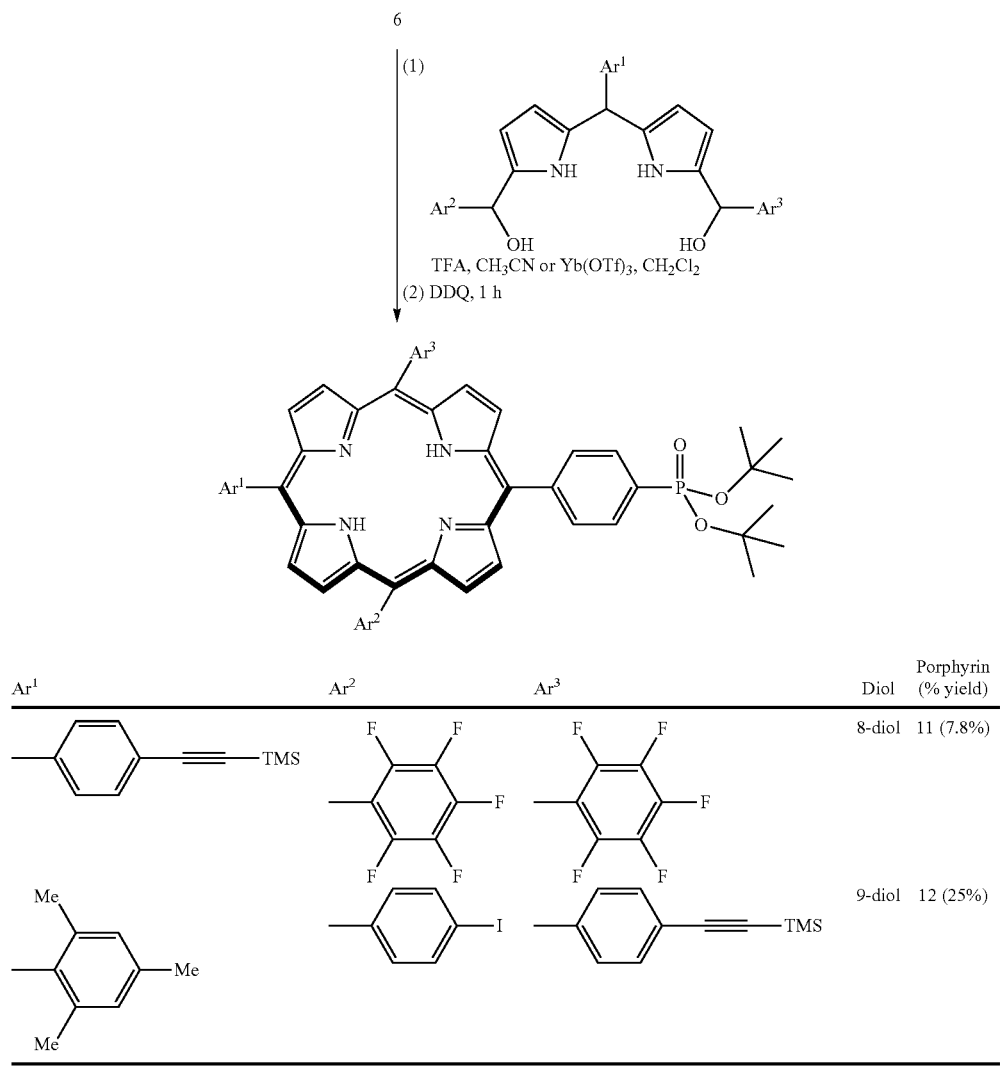

| Ar¹ | Ar² | Ar³ | Diol | Porphyrin (% yield) |
|---|---|---|---|---|
| 4-(TMS-ethynyl)phenyl | pentafluorophenyl | pentafluorophenyl | 8-diol | 11 (7.8%) |
| mesityl (2,4,6-trimethylphenyl) | 4-iodophenyl | 4-(TMS-ethynyl)phenyl | 9-diol | 12 (25%) |

Application of the procedure for monoacylation of a dipyrromethane[54] to 6 by treatment with EtMgBr and pyridyl thioester 13[54] or 14[52] gave the corresponding monoacyl product 15 or 16 in 48% or 69% yield, respectively (Scheme 6).

Scheme 6

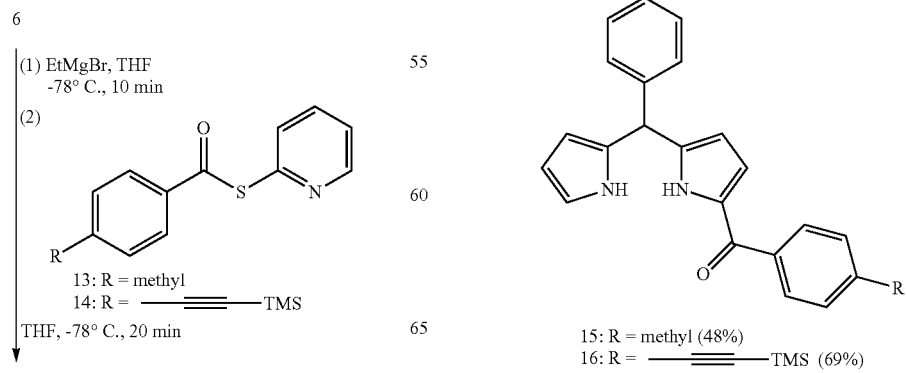

15: R = methyl (48%)
16: R = ─≡─TMS (69%)

Compound 15 on reduction with NaBH$_4$ in THF/methanol afforded the monocarbinol 15-OH. Self-condensation[54] of 15-OH on treatment with TFA in CH$_3$CN followed by oxidation with DDQ afforded the bis-phosphonate-porphyrin 17 in 28% yield (Scheme 7). The self-condensation of 15-OH using InCl$_3$ as catalyst[53] resulted in a very low yield (3%) of the required porphyrin 17.

Scheme 7

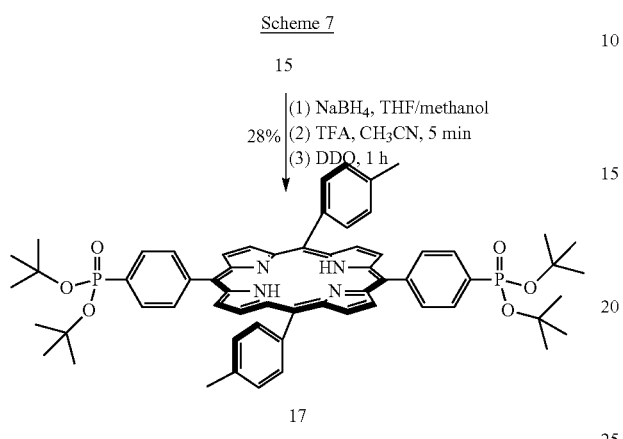

A chlorin bearing a phenylphosphonic acid tether also was prepared. Monoacyl-dipyrromethane 15 was treated with NBS to afford 18 in 78% yield. Reduction of 18 with NaBH$_4$ gave the monocarbinol 18-OH (Eastern half), which on reaction with tetrahydrodipyrrin 19[55] (Western half) under one-flask chlorin-forming conditions[55] gave the phosphonate-substituted zinc chlorin Zn20 in 17% yield (Scheme 8). Treatment of Zn20 with TMS—Cl/TEA in CHCl$_3$ at reflux afforded the zinc chlorin-phosphonic acid Zn21 in 88% yield.

Scheme 8

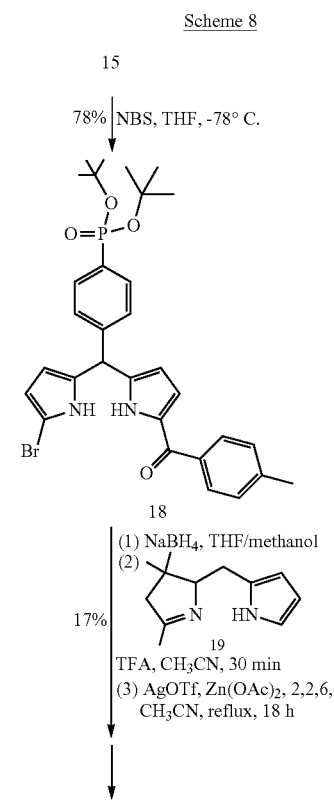

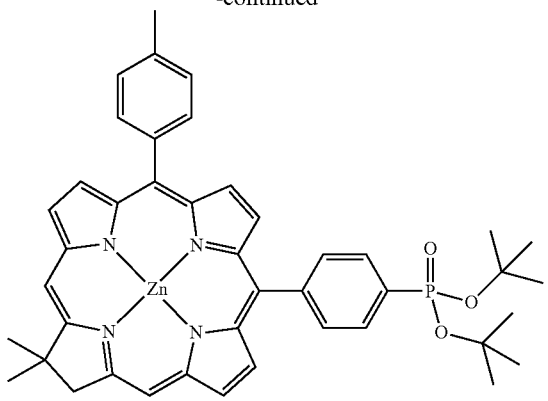

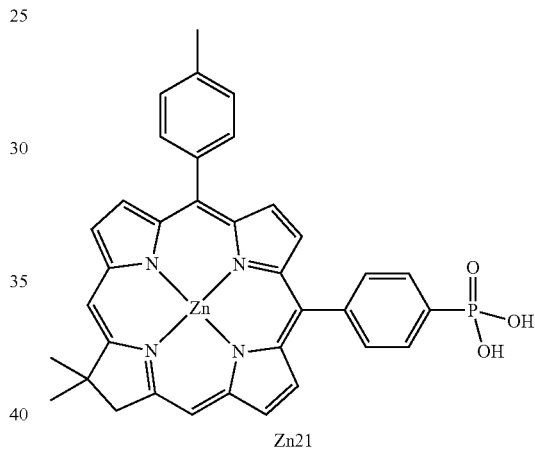

The synthesis of a porphyrin dyad bearing a single phosphonic acid tether is shown in Scheme 9. The synthesis employed Zn22[56] with Zn23; Zn23 was prepared by coupling of Zn(II)-5 dophenyl)-10,20-dimesityl-15-[4-[2-(trimethylsilyl)ethynyl]phenyl]porphyrin[57] and di-tert-butyl phosphite. The Sonogashira coupling of Zn22 with Zn23 was carried out under the conditions developed for synthesis of multiporphyrin arrays.[58] The conditions employ equimolar amounts of the two porphyrins in relatively dilute solution (5 mM each in toluene/TEA) at 35° C. with catalysis by Pd$_2$(dba)$_3$ and tri-o-tolylphosphine [P(o-tol)$_3$] without any copper cocatalysts. Thus, the coupling of Zn23 with Zn22 afforded Dyad-1 in 54% yield upon chromatographic workup including size exclusion chromatography[59] (SEC). Treatment of the dyad with TMS—Cl/TEA in refluxing CHCl$_3$ afforded Dyad-2 bearing a free phosphonic acid in 82% yield. No demetalation of the zinc porphyrins was observed.

Scheme 9

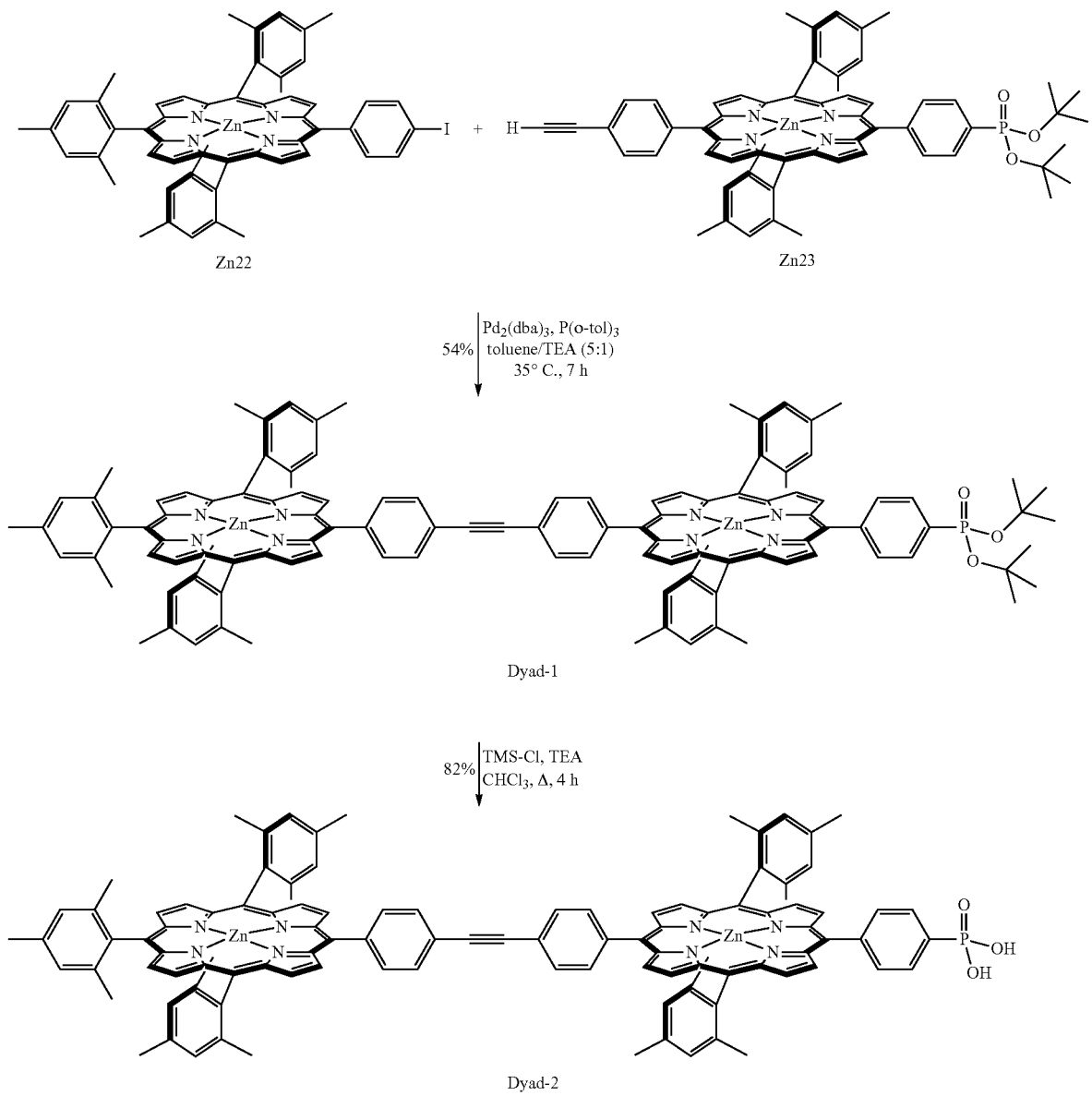

3. Characterization. The porphyrins and chlorins were characterized by absorption spectroscopy, $^1$H NMR spectroscopy, LDMS[60] and FABMS. The phosphonic acid/phosphonate-containing compounds were also characterized by $^{31}$P NMR spectroscopy using $H_3PO_4$ as an external standard. The $^{31}$P NMR spectrum of each of the phosphonate-containing compounds yielded a singlet. The $^1$H NMR and $^{13}$C NMR spectra of the molecules bearing phosphonate groups showed splitting of some signals originating from atoms in the adjacent phenylene or alkyl phosphonate unit due to coupling with the phosphorous nucleus. $^1$H NMR and $^{31}$P NMR spectra for Zn21 were not obtained (in $CDCl_3$, THF-$d_8$, $CD_3OD$, or DMSO-$d_6$) due to aggregation.

Example II

The ability to attach redox-active molecules to oxide surfaces in controlled architectures (distance, orientation, packing density) is essential for the design of a variety of molecular-based information storage devices. We describe the synthesis of a series of redox-active molecules wherein each molecule bears a benzylphosphonic acid tether. The redox-active molecules include zinc porphyrins and a cobalt(II) porphyrin. An analogous tripodal tether has been prepared that is based on a tris-[4-(dihydroxyphosphorylmethyl)phenyl]-derivatized methane. A zinc porphyrin is linked to the methane vertex by a 1,4-phenylene unit. The tripodal systems are designed to improve monolayer stability and ensure vertical orientation of the redox-active porphyrin on the electroactive surface. For comparison purposes, a zinc porphyrin bearing a hexylphosphonic acid tether also has been prepared. The synthetic approaches for introduction of the phosphonic acid group include derivatization of a bromoalkyl porphyrin or use of a dimethyl or diethyl phosphonate-substituted precursor in a porphyrin-forming reaction. The latter approach makes use of dipyrromethane building blocks bearing mono or tripodal dialkyl phosphonate groups. Collectively, a variety of porphyrinic molecules can now be prepared with tethers of different length, composition, and structure (mono or tripodal) for studies of molecular-based information storage on oxide surfaces.

1. Synthesis. Zinc Porphyrins Bearing Single Tethers. (a) Benzylphosphonic Acid Tethers. Porphyrin 24 was treated with $Zn(OAc)_2 \cdot 2H_2O$ to afford Zn24 in 94% yield (Scheme 10). Treatment of Zn24 to the same conditions described in Example I to cleave di-tert-butyl groups [TMS—Br (15 equiv) and TEA (20 equiv) in refluxing $CHCl_3$] caused cleavage of the ethyl protecting groups to afford porphyrin-benzylphosphonic acid Zn25 in 78% yield.

cleaved under the same conditions employed for Zn24, affording porphyrin Zn25 in 77% yield. Based on this single comparison, the methyl and ethyl protecting groups seem comparable in affording the corresponding porphyrin-phosphonic acid.

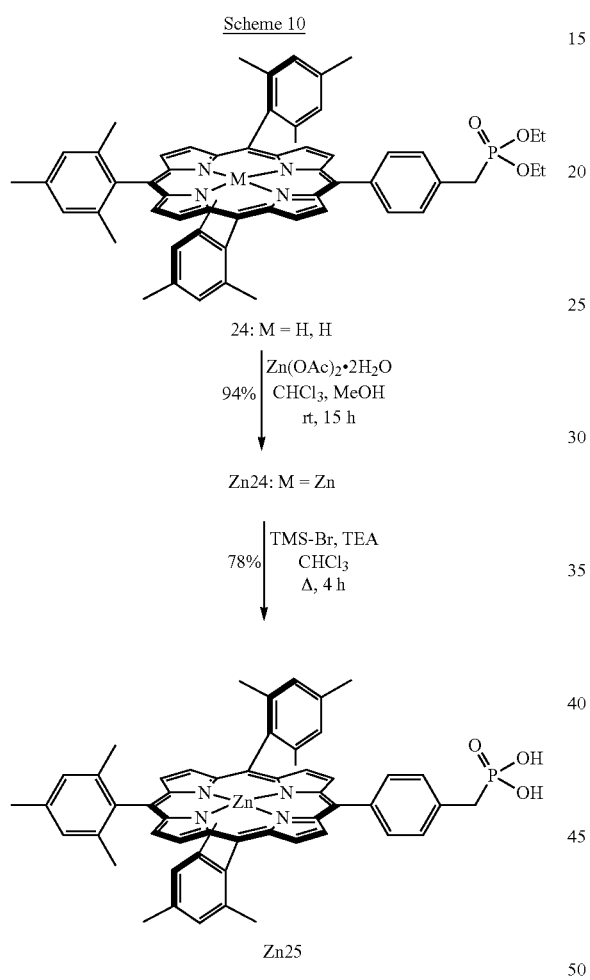

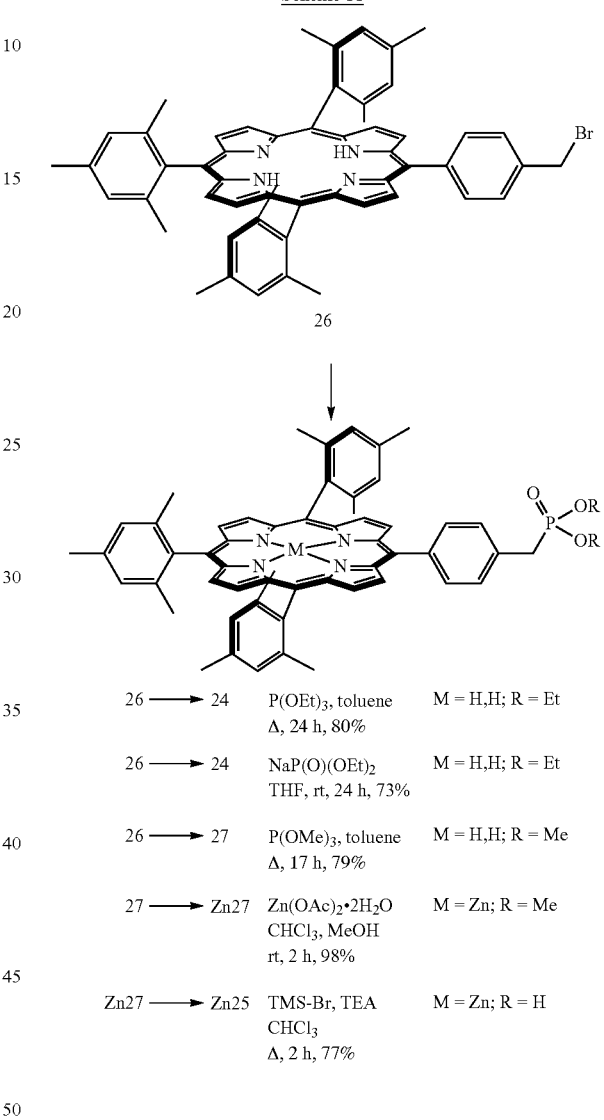

Porphyrin 24 could also be prepared following the approaches shown in Scheme 11. The mixed-aldehyde condensation[47] at high concentration[61] of 4-bromomethylbenzaldehyde,[62] mesitaldehyde, and pyrrole with $BF_3 \cdot O(Et)_2$-ethanol cocatalysis[48] followed by oxidation with DDQ afforded the porphyrin (26) that bears one bromomethyl group. Porphyrin 26 is a valuable porphyrin building block. As with other bromomethylporphyrins,[63] 26 can be functionalized with a wide variety of nucleophiles. For example, treatment of 26 with triethyl phosphite in an Arbuzov reaction, or sodium diethyl phosphite in THF, gave porphyrin 24 in 80% or 73% yield, respectively. Both routes afford porphyrin 24 in a straightforward manner. Porphyrin 26 could also be treated with trimethyl phosphite in an Arbuzov reaction affording porphyrin 27 in 79% yield. Zinc insertion afforded porphyrin Zn27 in 98% yield. The methyl groups were The synthesis of a porphyrin-phosphonic acid bearing p-tolyl groups at all non-linking meso positions is shown in Scheme 12. The synthesis relies on the rational condensation of a dipyrromethane and a dipyrromethane-dicarbinol.[52] Reaction of 4-(diethoxyphosphorylmethyl)benzaldehyde (28) with excess pyrrole under TFA catalysis afforded dipyrromethane 29 in 46% yield. The condensation of 29 and 30-diol[64] in $CH_2Cl_2$ using $InCl_3$ as catalyst[53] followed by oxidation with DDQ afforded the free base porphyrin. The reaction of crude free base porphyrin with $Zn(OAc)_2 \cdot 2H_2O$ gave the zinc porphyrin Zn31. However, the insolubility of Zn31 in typical solvents ($CHCl_3$, THF, toluene and mixtures thereof) prevented analysis. A suspension of Zn31 in $CH_2Cl_2$ was treated with TFA, affording the free base porphyrin 31 in 12% overall yield. Free base porphyrin 31 showed good solubility and was readily characterized.

Scheme 12

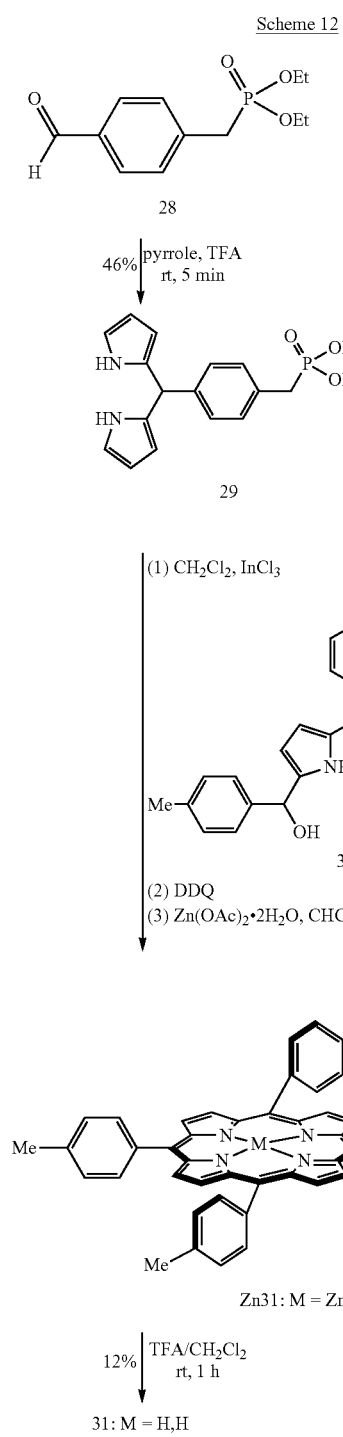

Scheme 13

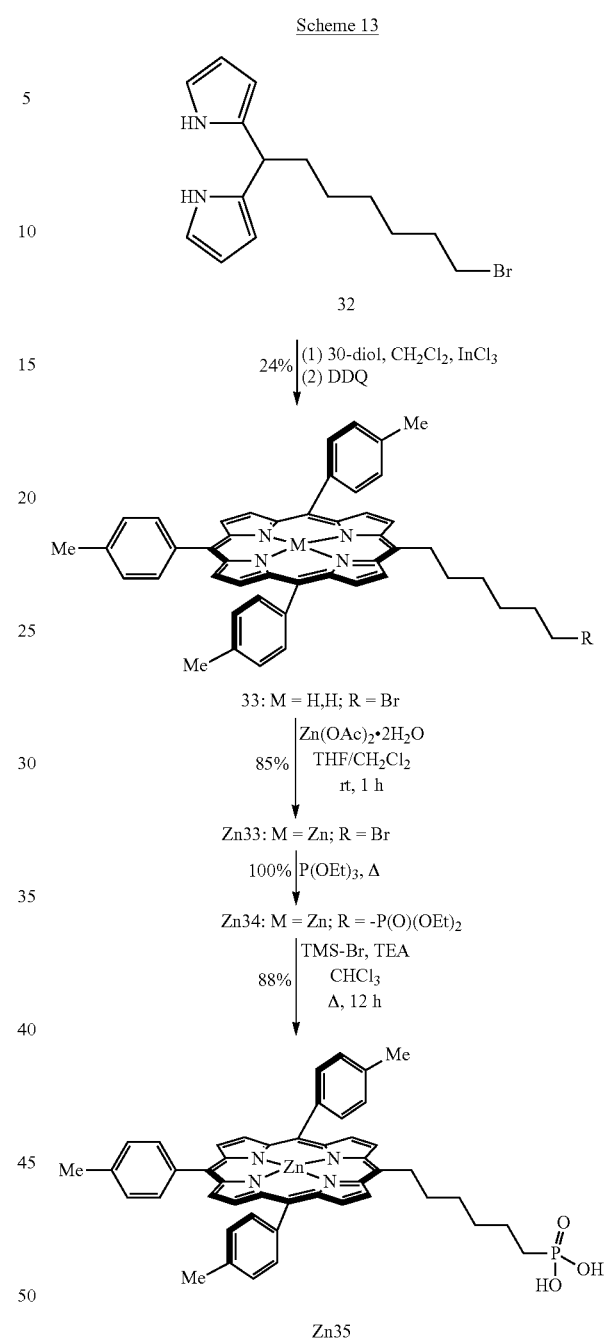

(b) Hexylphosphonic Acid Tether. To explore the effect of tether length on the electron-transfer properties of porphyrin SAMs, we prepared a porphyrin that bears a hexylphosphonic acid tether (Scheme 13). Condensation of dipyrromethane 32[65] and 30-diol using $InCl_3$ followed by oxidation with DDQ afforded porphyrin 33 in 24% yield. Metalation furnished Zn33 in 85% yield. An Arbuzov reaction of Zn33 and triethylphosphite afforded porphyrin Zn34 in quantitative yield. Treatment with TMS—Br/TEA in refluxing $CHCl_3$ gave porphyrin-hexylphosphonic acid Zn35 in 88% yield.

Porphyrin Architectures for Increased Memory Density. Molecules with an increased number of cationic oxidation states can afford increased memory density. We have explored the use of cobalt(II) porphyrins to serve as molecules that can provide three cationic oxidation states: the mono- and dication porphyrin radicals and a metal-centered Co(II)/Co(III)[66] oxidation. The synthesis of a cobalt porphyrin-phosphonic acid is shown in Scheme 14. Porphyrin 24 was treated with $Co(OAc)_2$ to yield the cobalt porphyrin Co24 in 68% yield. Cleavage of the ethyl protecting groups using the same procedure described above (TMS—Br/TEA in refluxing $CHCl_3$) furnished the porphyrin-phosphonic acid Co25 in 92% yield.

Scheme 14

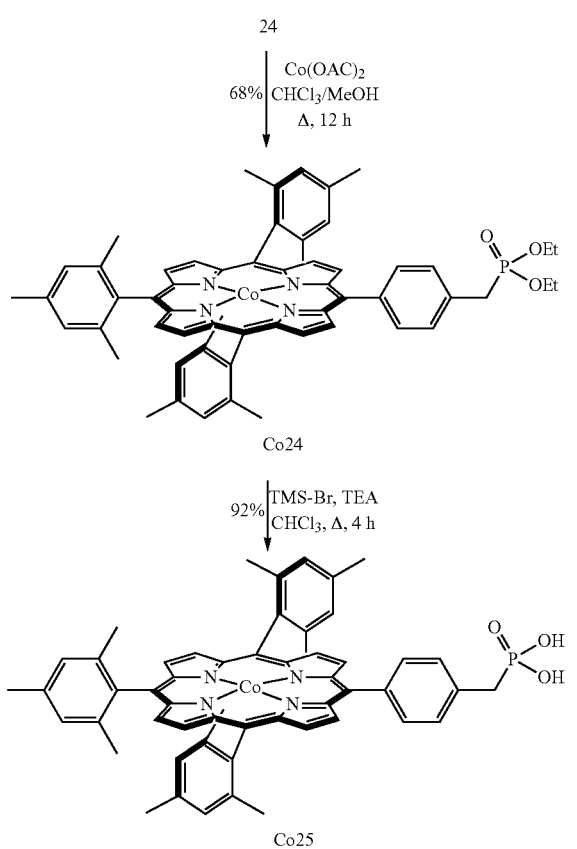

Porphyrins Bearing Tripodal Phosphonic Acid Tethers.

Our design for porphyrins bearing tripodal phosphonic acid tethers incorporates a p-phenylene group between the porphyrin and the methane-carbon vertex of the tripod. The three legs of the tripod are provided by benzylphosphonic acid groups. The synthesis we developed proceeds via a dipyrromethane bearing the tripod with protected phosphonic acid groups (Scheme 15).

Scheme 15

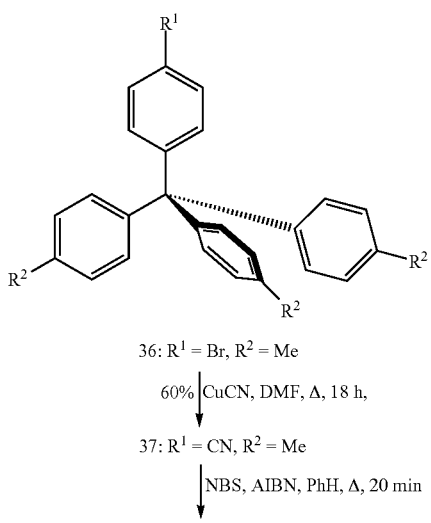

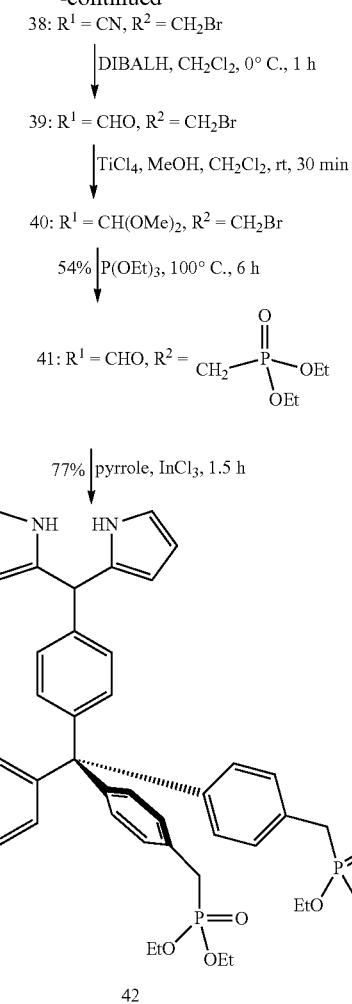

The synthesis begins with 1-(4-bromophenyl)-1,1,1-tri-p-tolylmethane (36).[27] Rosenmund-von Braun reaction of 36 with CuCN afforded 37 in 60% yield (76% based on recovery of starting material 36). Radical bromination of 37 using NBS (1.1 eq per methyl group) and AIBN in refluxing benzene furnished crude tribromo nitrile 38 in ~90% purity. $^1$H NMR spectroscopy showed the presence of unreacted p-tolyl resonances, indicating incomplete bromination. The mono and dibromo products were not easily removed from the reaction mixture; thus, the crude material was carried forward. Reduction of crude 38 with DIBALH gave aldehyde 39, which was converted to the acetal (40) using $TiCl_4$ in $CH_2Cl_2$/methanol. Subsequent reaction with triethylphosphite at 100° C. for 6 h afforded 41 in 54% yield (from 37). The acetal was cleaved during the acidic workup that was employed to convert the odorous triethylphosphite to diethylphosphite. While each member of the series of compounds 38-40 was ~90% pure owing to the presence of partially brominated species, 41 was obtained in pure form. Condensation of 41 with excess pyrrole under new reaction conditions ($InCl_3$ as catalyst)[67] afforded dipyrromethane 42 in 77% yield.

Dipyrromethane 42 serves as a valuable synthetic intermediate for condensation with dipyrromethane-dicarbinols[52] to afford porphyrins bearing a tripodal phosphonate tether. Thus, condensation of 42 and dipyrromethane-dicarbinol 30-diol[64] with catalysis by $InCl_3$ followed by oxidation with DDQ gave the free base porphyrin. Metalation gave zinc porphyrin Zn44 in 11.3% overall yield. Deprotection using 5 equiv of TMS—Br and 6.7 equiv of TEA per phosphonate group afforded porphyrin Zn46 in 82% yield (Scheme 16).

Scheme 16
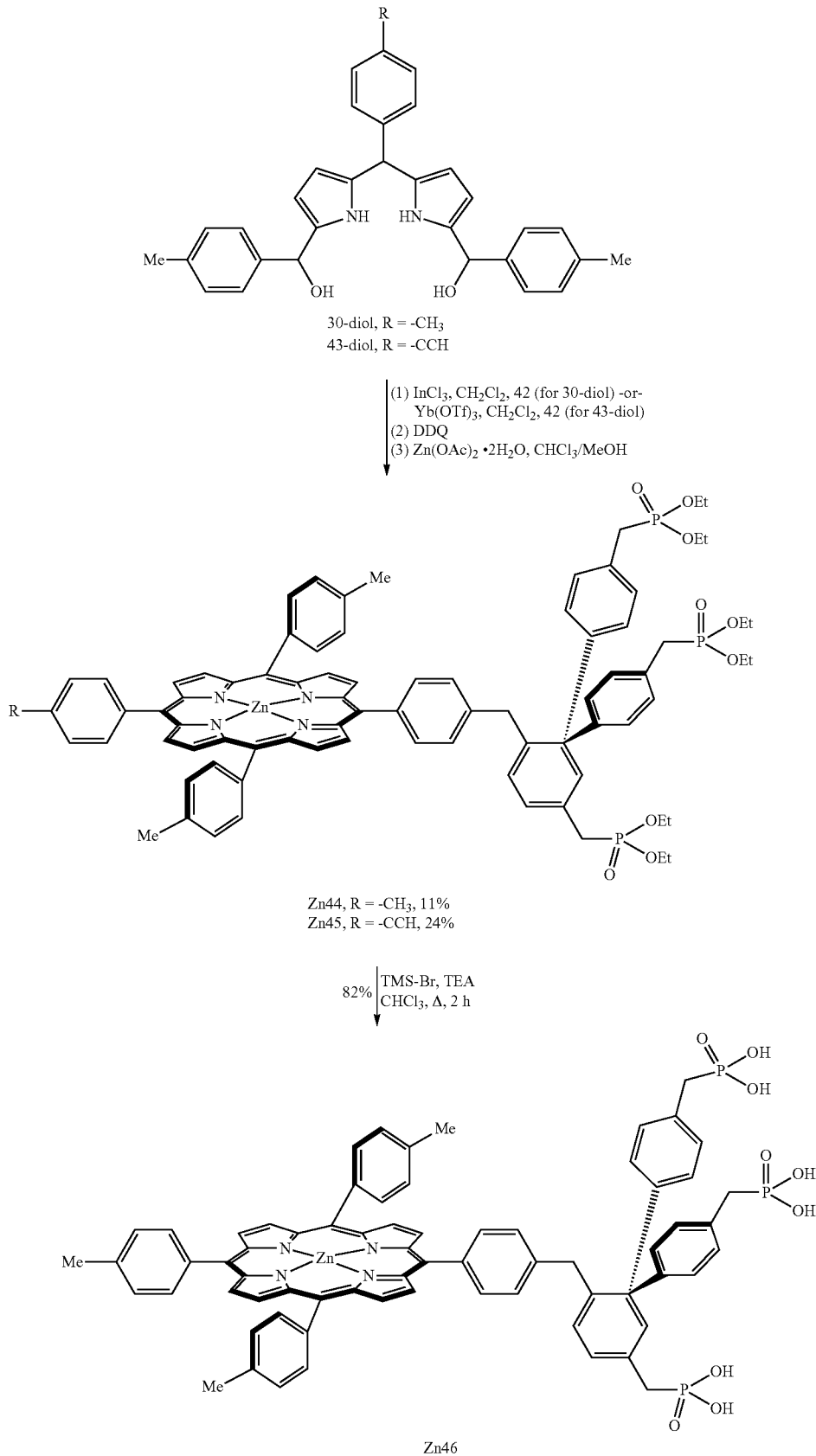

Similarly, a porphyrin was prepared that bears a free ethynyl group for Sonogashira oligomerization with porphyrin monomers. The ethynyl unit was incorporated via 43-diol. The condensation of 42 and 43-diol in $CH_2Cl_2$ with $Yb(OTf)_3$ as catalyst[53] followed by oxidation with DDQ gave the free base porphyrin. Metalation afforded zinc porphyrin Zn45 in 24% yield (Scheme 16).

2. Chemical Characterization and Solubility Properties. All porphyrins were characterized by absorption spectroscopy, $^1H$ NMR spectroscopy, LDMS and FABMS. The phosphonate-containing compounds generally were also characterized by $^{31}P$ NMR spectroscopy using $H_3PO_4$ as an external standard. In a few cases, solubility limited purification and analysis. Tri-p-tolylporphyrin Zn31 was sparingly soluble ($CHCl_3$, THF, or toluene) while trimesitylporphyrin Zn24 displayed good solubility in these solvents. The greater bulk of the mesityl versus p-tolyl group suppresses cofacial aggregation between porphyrins. The free base analogs of both these porphyrins display good solubility. The limited solubility of Zn31 but not its free base analog is attributed to coordination of the dialkyl phosphonate of one porphyrin to the apical site of the zinc porphyrin of another porphyrin. Each porphyrin bearing a tripodal phosphonate tether displayed good solubility in common organic solvents. Porphyrin Zn46, which bears three phosphonic acid groups, was quite soluble in water as well as organic solvents.

Experimental Section

General. $^1H$ NMR (400 MHz) and $^{13}C$ NMR (100 MHz) spectra were recorded in $CDCl_3$ unless noted otherwise. Mass spectra of porphyrinic compounds were obtained by FABMS, laser desorption mass spectrometry in the absence of a matrix (LDMS), and/or MALDI-MS using the matrix 1,4-bis(5-phenyloxazol-2-yl)benzene (POPOP). Absorption and emission spectra were collected in toluene at room temperature unless noted otherwise. Melting points are uncorrected. Silica gel (40 μm average particle size) was used for column chromatography. Alumina activity grade I was deactivated to grade V for chromatography of magnesium-porphyrinic compounds. Phosphoric acid ($H_3PO_4$) was used as external standard (referenced to δ 0.00 ppm) for $^{31}P$ NMR (161.98 MHz) spectroscopy. Preparative SEC was performed as described previously.[59] All Pd-mediated coupling reactions were carried out under argon using standard Schlenk techniques.[58]

Non-Commercial Compounds. 4-Bromobenzaldehyde dimethylacetal,[46] 4-bromomethylbenzaldehyde,[62] Zn(II)-5-(4-iodophenyl)-10,20-dimesityl-15-[4-[2-(trimethylsilyl)ethynyl]phenyl]porphyrin,[57] 5-[4-(2-trimethylsilyl)ethynylphenyl)-1,9-bis(4-methylbenzoyl)dipyrromethane,[68] 5,[51] 7-9,[52] 13,[54] 14,[54] 19,[55] Zn22,[56] 30,[64] 32,[65] and 36[27] were synthesized according to literature procedures.

Solvents. Toluene and TEA were freshly distilled from $CaH_2$ and sparged of oxygen prior to use. THF was distilled from sodium. $CH_3CN$ was distilled from $CaH_2$ and stored over molecular sieves. All other solvents were used as received. $CHCl_3$ stabilized with 0.8% ethanol was used for the porphyrin-forming reactions and chromatography procedures. $CHCl_3$ stabilized with amylenes (not ethanol) was used for the cleavage of dialkyl phosphonates.

4-(Di-tert-butyloxyphosphoryl)benzaldehyde dimethylacetal. Samples of 4-bromobenzaldehyde dimethylacetal (5.0 g, 22 mmol) and di-tert-butylphosphite (5.1 g, 27 mmol) were coupled using $Pd(PPh_3)_4$ (1.3 g, 1.1 mmol) in toluene/TEA [10 mL, (1:1)] at 80° C. under argon for 20 h. A precipitate was formed during the course of the reaction. The reaction mixture was filtered and the filtrate was concentrated. Column chromatography [silica, hexanes/ethyl acetate (8:2)→ethyl acetate/MeOH (9:1)] afforded a yellow oil (4.00 g, 53%): by 152° C.; $^1H$ NMR δ 1.46 (s, 18 H), 3.34 (s, 6H), 5.41 (s, 1H), 7.48-7.52 (m, 2H), 7.76-7.83 (m, 2H); $^{13}C$ NMR δ 30.8, 30.9, 52.7, 82.3, 82.4, 103.4, 127.3, 127.4, 132.1, 132.2, 142.6, 142.7; $^{31}P$ NMR (THF-$d_8$) δ 10.6; Anal. Calcd for $C_{17}H_{29}O_5P$: C, 59.29; H, 8.49. Found: C, 59.18; H, 8.49.

5-[4-(Di-tert-butyloxyphosphoryl)phenyl]-10,15,20-trimesitylporphyrin (1). Samples of mesitaldehyde (1.34 g, 9.00 mmol), 4-(di-tert-butyloxyphosphoryl)benzaldehyde dimethylacetal (1.00 g, 3.00 mmol), and pyrrole (805 mg, 12.0 mmol) were condensed in $CHCl_3$ (1.2 L) containing ethanol as a stabilizer was treated with $BF_3 \cdot O(Et)_2$ (500 μL) at room temperature for 1.5 h. DDQ (2.04 g, 9.00 mmol) was added. After 1 h, TEA was added and the reaction mixture was concentrated. Column chromatography [silica, $CHCl_3$/hexanes (1:1)→$CHCl_3$/ethyl acetate (8:2); silica, $CHCl_3$/ethyl acetate (8:2)] afforded a purple solid (255 mg, 6.8%): $^1H$ NMR δ −2.58 (br s, 2H), 1.65 (s, 18H), 1.84-1.85 (m, 18H), 2.62 (s, 9H), 7.27 (s, 6H), 8.14-8.27 (m, 4H), 8.64-8.73 (m, 8H); $^{31}P$ NMR (THF-$d_8$) δ 10.7; LDMS obsd 934.0, 877.2 [(M−tert-Bu)$^+$]; 821.01 [(M−2×tert-Bu)$^+$]; FABMS obsd 932.4788; calcd 932.4794 ($C_{61}H_{65}N_4O_3P$); $\lambda_{abs}$ 420, 514, 547, 592, 650 nm; $\lambda_{em}$ ($\lambda_{ex}$=550) 650, 719 nm.

Zn(II)-5-[4-(Di-tert-butyloxyphosphoryl)phenyl]-10,15-20-trimesitylporphyrin (Zn1). A solution of 1 (0.210 g, 0.225 mmol) in $CHCl_3$ (50 mL) was treated overnight with $Zn(OAc)_2 \cdot 2H_2O$ (0.250 g, 1.14 mmol) in methanol (5 mL) at room temperature. The reaction mixture was washed with water, dried ($Na_2SO_4$) and chromatographed [silica, $CHCl_3$/ethyl acetate (9:1)] to afford a purple solid (163 mg, 73%): $^1H$ NMR δ 1.64 (s, 18H), 1.84 (s, 18H), 2.62 (s, 9H), 7.27 (s, 6H), 8.07-8.28 (m, 4H), 8.64-8.75 (m, 8H); $^{31}P$ NMR (THF-$d_8$) δ 11.1; LDMS obsd 993.5, 881.9 [(M−2×tert-Bu)$^+$]; FABMS obsd 994.3925; calcd 994.3929 ($C_{61}H_{63}N_4O_3PZn$); $\lambda_{abs}$ 423, 550 nm; $\lambda_{em}$ ($\lambda_{ex}$=550 nm) 600, 649 nm.

Zinc(II)-5-[4-(Diethoxyphosphoryl)phenyl]-10,15,20-trimesitylporphyrin (Zn3). A solution of porphyrin 3 (0.080 g, 0.090 mmol) in $CHCl_3$/methanol (8:1) was treated overnight with $Zn(OAc)_2 \cdot 2H_2O$ (0.099 g, 0.45 mmol). Standard workup including chromatography [silica, $CHCl_3$/methanol (98:2)] afforded a purple solid (0.071 g, 85%): $^1H$ NMR δ 1.17 (t, J=7.2 Hz, 6 H), δ 1.80-1.88 (m, 18H), 2.58-2.65 (m, 9H), 3.60-3.75 (m, 4H), 7.28 (s, 6H), 7.43-7.55 (m, 2H), 8.12-8.21 (m, 2H), 8.65-8.78 (m, 8H); LDMS obsd 937.9; FABMS obsd 938.3339, calcd 938.3303 ($C_{57}H_{55}N_4O_3PZn$); $\lambda_{abs}$ 423, 549 nm.

Mg(II)-5-[4-(Di-tert-butyloxyphosphoryl)phenyl]-10,15-20-trimesitylporphyrin (Mg1). A solution of 1 (23 mg, 0.025 mmol) in $CH_2Cl_2$ (1 mL) was treated with the ethereal $MgI_2$-DIEA reagent (7 mL, ~0.04 M solution of $MgI_2$) and the mixture was stirred at room temperature for 1 h. The mixture was diluted with $CH_2Cl_2$ and washed with aqueous 5% $NaHCO_3$ and water, dried ($Na_2SO_4$) and concentrated. Trituration with hexanes afforded a purple solid (17 mg, 71%): $^1H$ NMR (THF-$d_8$) δ 1.63 (s, 18H), 1.82-1.89 (m, 18H), 2.58-2.63 (s, 9H), 7.27 (s, 6H), 8.05-8.15 (m, 2H), 8.21-8.29 (m, 2H), 8.52-8.56 (m, 6H), 8.63-8.66 (m, 2H); $^{31}P$ NMR (THF-dg) δ 11.31; LDMS obsd 956.3, 901.2 [(M−tert-Bu)$^+$], 843.8 [(M−2×tert-Bu)$^+$]; FABMS obsd 954.4443; calcd 954.4488 ($C_{61}H_{63}MgN_4O_3P$); $\lambda_{abs}$ (THF) 431, 573, 614 nm.

5-(4-Dihydroxyphosphorylphenyl)-10,15,20-trimesitylporphyrin (2). A sample of Zn3 (175 mg, 0.200 mmol) in $CH_2Cl_2$ (20 mL) was treated with 16 equiv of TMS—Br (0.420 mL, 3.20 mmol). The green mixture was stirred overnight at room temperature. The solvent was evaporated to afford a green residue. The green residue was suspended in water and the suspension was stirred at room temperature for 2 h. The mixture was extracted with $CHCl_3$. The $CHCl_3$ layer was washed with saturated aqueous $NaHCO_3$, water and dried ($Na_2SO_4$). The solution was concentrated. Chromatography [silica, $CHCl_3$/MeOH (1:1)] afforded a purple solid (130 mg, 79%): $^1H$ NMR δ −2.74 (br s, 2H), 1.76 (s, 18H), 2.57 (s, 9H), 7.12-7.26 (m, 4H), 7.32 (s, 2H), 8.04-8.16 (m, 4H), 8.46-8.62 (m, 6H), 8.74-8.82 (m, 2H); LD-MS obsd 820.9; FAB-MS obsd 820.3560, calcd 820.3542 ($C_{53}H_{49}N_4O_3P$); $\lambda_{abs}$ (THF) 419, 515, 550, 592, 648 nm.

Zn(II)-5-[4-(Dihydroxyphosphoryl)phenyl]-10,15,20-trimesitylporphyrin (Zn2; from Zn1). A mixture of Zn1(150 mg, 0.150 mmol), TMS—Cl (287 μL, 2.25 mmol) and TEA (300 μL, 3 mmol) in CHCl$_3$ (15 mL) was stirred at reflux (~65° C.) under argon for 4 h. The reaction mixture was washed with water, dried (Na$_2$SO$_4$) and chromatographed [silica, CHCl$_3$/ethyl acetate (1:1)→CHCl$_3$/MeOH (1:1)] to afford a purple solid (118 mg, 89%): $^1$H NMR δ 1.70-1.76 (m, 18H), 2.50-2.51 (m, 9H), 7.20-7.26 (m, 6H), 8.10-8.11 (m, 2H), 8.28-8.29 (m, 2H), 8.50-8.51 (m, 6H), 8.70-8.71 (m, 2H); $^{31}$P NMR (THF-d$_8$) δ 12.2; LDMS obsd 885.70; FABMS obsd 881.49; calcd 882.27 (C$_{53}$H$_{47}$N$_4$O$_3$PZn); λ$_{abs}$ 420, 550 nm; λ$_{em}$ 596, 645 nm.

Zn2 from Zn3. A mixture of Zn3 (30 mg, 0.032 mmol), TMS—Br (66 μL, 0.50 mmol) and TEA (66 μL, 0.63 mmol) in CHCl$_3$ (4 mL) was stirred at reflux for 4 h. The reaction mixture was diluted with CH$_2$Cl$_2$ (100 mL), washed with water, dried (Na$_2$SO$_4$) and chromatographed [silica, CHCl$_3$/ethyl acetate (1:1)→CHCl$_3$/MeOH (1:1)] to afford a purple solid (23 mg, 81%). Characterization data were consistent with those reported above.

Zn2 by metalation of 2. A solution of porphyrin 2 (0.123 g, 0.150 mmol) in CHCl$_3$/methanol (15 mL, 2:1) was treated overnight with Zn(OAc)$_2$.2H$_2$O (0.329 g, 1.50 mmol). Standard workup including chromatography [silica, CHCl$_3$/MeOH (1:1)] afforded a purple solid (0.103 g, 77%). Characterization data were consistent with those reported above.

Mg(II)-5-[4-(Dihydroxyphosphoryl)phenyl]-10,15,20-trimesitylporphyrin (Mg2). A sample of Mg1 (14 mg, 0.015 mmol) in CHCl$_3$ (5 mL) was treated with TEA (0.041 mL, 0.30 mmol) and TMS—Br (0.030 mL, 0.23 mmol). The cloudy mixture was stirred at reflux for 4 h. Water was added and the mixture was extracted with CHCl$_3$. The organic layer was dried (Na$_2$SO$_4$) and concentrated. Trituration with hexanes afforded a purple solid (10 mg, 77%): $^1$H NMR (THF-d$_8$) δ 1.75-1.90 (m, 18H), 2.50-2.70 (m, 9H), 7.15-7.35 (m, 6H), 8.10-8.35 (m, 4H), 8.45-8.62 (m, 6H), 8.68-8.82 (m, 2H); $^{31}$P NMR (THF-d$_8$) δ 14.37; MALDI-MS (POPOP) obsd 843.5, 821.5 [(M−Mg)$^+$]; FABMS obsd 842.3239; calcd 842.3236 (C$_{53}$H$_{47}$MgN$_4$O$_3$P); λ$_{abs\ (THF)}$ 431, 574, 614 nm.

5-[4-(Di-tert-butyloxyphosphoryl)phenyl]dipyrromethane (6). Method A: A solution of 4 (3.44 g, 10.0 mmol) and pyrrole (17.4 mL, 0.250 mol) in CH$_2$Cl$_2$ (20 mL) was treated with TFA (77 μL, 1.0 mmol) under argon for 2 h at room temperature. Then 0.1 M NaOH was added. The mixture was poured into brine and ethyl acetate. The organic phase was isolated, washed with water, dried (Na$_2$SO$_4$) and concentrated. Column chromatography [silica, CH$_2$Cl$_2$/ethyl acetate (3:1)] afforded an orange oil. Recrystallization [ethanol/water (1:1)] afforded a pale brown powder (1.3 g, 31%): mp 138-139° C.; $^1$H NMR δ 1.44 (s, 18H), 5.51 (s, 1H), 5.93 (s, 2H), 6.13-6.15 (m, 2H), 6.69-6.71 (m, 2H), 7.13-7.22 (m, 2H), 7.52-7.62 (m, 2H), 8.68 (br s, 2H); $^{13}$C NMR δ 30.46, 30.50, 43.9, 82.61, 82.68, 107.4, 107.9, 117.7, 128.1, 128.2, 130.2, 131.4, 131.5, 132.05, 132.11, 146.49, 146.52; $^{31}$P NMR δ 10.94; Anal. Calcd for C$_{23}$H$_{31}$N$_2$O$_3$P: C, 66.65; H, 7.54; N, 6.76. Found: C, 66.57; H, 7.41; N, 6.65.

Method B: Samples of 5 (1.0 g, 3.4 mmol) and Pd(PPh$_3$)$_4$ (200 mg, 0.17 mmol) in TEA (1 mL) and toluene (1 mL) was treated with di-tert-butylphosphite (740 mg, 3.8 mmol). The reaction mixture was stirred under argon at 85° C. for 20 h, then concentrated and chromatographed [silica, CHCl$_3$/ethyl acetate (3:1)] to afford a light brown solid (600 mg, 43%). Characterization data were consistent with those described above.

5,15-Bis(pentafluorophenyl)-10-[4-(di-tert-butyloxyphosphoryl)phenyl]-20-(4-iodophenyl)porphyrin (10). A solution of 7 (888 mg, 1.21 mmol) in THF/methanol [55 mL (10:1)] was treated with NaBH$_4$ (915 mg, 24.2 mmol). The resulting dipyrromethane-dicarbinol (7-diol) was condensed with 6 (0.500 g, 1.21 mmol) in CH$_2$Cl$_2$ (484 mL) containing Yb(OTf)$_3$ (954 mg, 1.53 mmol, 3.2 mM). After 20 min, a sample of DDQ (824 mg, 3.63 mmol) was added. After 30 min, TEA was added followed by filtration through a silica pad [CH$_2$Cl$_2$/ethyl acetate (5:1)]. Column chromatography [silica, CHCl$_3$/MeOH (98:2)] followed by trituration with methanol afforded a purple solid (62 mg, 4.6%): $^1$H NMR δ −2.88 (br s, 2H), 1.68 (s, 18H), 7.95 (d, J=6.8 Hz, 2H), 8.13 (d, J=6.8 Hz, 2H), 8.19-8.29 (m, 4H), 8.82-8.83 (m, 4H), 8.91 (d, J=4.8 Hz, 2H), 8.94 (d, J=4.8 Hz, 2H); LDMS obsd 1114.1, 1058.0 [(M−tert-Bu)$^+$], 1000.9 [(M−2×tert-Bu)$^+$]; FABMS obsd 1112.1429; calcd 1112.1410 (C$_{52}$H$_{36}$F$_{10}$IN$_4$O$_3$P). λ$_{abs}$ 419, 512, 544, 589, 643 nm; λ$_{em}$ (λ$_{ex}$=513 nm) 647, 715 nm.

5,15-Bis(pentafluorophenyl)-10-[4-(di-tert-butyloxyphosphoryl)phenyl]-20-[4-(2-(trimethylsilyl)ethynyl)phenyl]porphyrin (11). A solution of 8 (1.02 g, 1.45 mmol) in THF/methanol [55 mL (10:1)] was treated with NaBH$_4$ (1.10 g, 29.0 mmol). The resulting dipyrromethane-dicarbinol (8-diol) was condensed with 6 (600 mg, 1.45 mmol) in CH$_3$CN (580 mL) containing TFA (1.34 mL, 17.4 mmol, 30 mM). After 6 min, a sample of DDQ (824 mg, 3.63 mmol) was added. After 30 min, TEA was added and the mixture was filtered through a silica pad [CH$_2$Cl$_2$/ethyl acetate (5:1)]. The porphyrin-containing fractions (which contained a large amount of dipyrrin) were combined and concentrated. Trituration with methanol followed by filtration afforded a purple solid (123 mg, 7.8%): $^1$H NMR δ −2.86 (br s, 2H), 0.39 (s, 9H), 1.68 (s, 18H), 7.90 (d, J=7.6 Hz, 2H), 8.17 (d, J=7.6 Hz, 2H), 8.19-8.29 (m, 4H), 8.83-8.84 (m, 4H), 8.91-8.94 (m, 4H); $^{31}$P NMR δ 10.14; LDMS obsd 1083.7, 1027.7 [(M−tert-Bu)$^+$], 971.4 [(M−2×tert-Bu)$^+$]; FABMS obsd 1082.2810; calcd 1082.2839 (C$_{57}$H$_{45}$F$_{10}$N$_4$O$_3$PSi). λ$_{abs}$ 419, 512, 545, 589, 644 nm; λ$_{em}$ (λ$_{ex}$=512 nm) 648, 715 nm.

5-[4-(Di-tert-butyloxyphosphoryl)phenyl]-10-(4-iodophenyl)-15-mesityl-20-[4-(2-(trimethylsilyl)ethynyl)phenyl]porphyrin (12). A solution of 9 (0.347 g, 0.500 mmol) in THF/methanol [33 mL (10:1)] was treated with NaBH$_4$ (0.380 g, 10.0 mmol). The resulting dipyrromethane-dicarbinol (9-diol) was condensed with 6 (0.207 g, 0.500 mmol) in CH$_3$CN (200 mL) containing TFA (0.460 mL, 6.00 mmol, 30 mM). After 5 min, a sample of DDQ (0.340 mg, 1.50 mmol) was added. After 1 h, TEA was added and the mixture was filtered through a silica pad [CHCl$_3$/ethyl acetate (95:5)]. The porphyrin-containing fractions were combined, concentrated and chromatographed [silica, CHCl$_3$/ethyl acetate (90:10) to afford a purple solid (127 mg, 25%): $^1$H NMR δ −2.73 (br s, 2H), 0.39 (s, 9H), 1.68 (s, 18H), 1.84 (s, 6H), 2.64 (s, 3H), 7.29 (s, 2H), 7.88 (d, J=8.4 Hz, 2H), 7.96 (d, J=8.4 Hz, 2H), 8.09 (d, J=8.4 Hz, 2H), 8.15-8.30 (m, 6H), 8.70-8.75 (m, 2H), 8.76-8.90 (m, 6H); $^{31}$P NMR δ 10.14; LDMS obsd 1072.2, 960.7 [(M−tert-Bu)$^+$], 834.3 [(M−2×tert-Bu−I)$^+$]; FABMS obsd 1070.3202; calcd 1070.3217 (C$_{60}$H$_{60}$IN$_4$O$_3$PSi). λ$_{abs}$ 422, 515, 550, 592, 648 nm.

5-[4-(Di-tert-butyloxyphosphoryl)phenyl]-1-p-toluoyldipyrromethane (15). A solution of EtMgBr (5 mL, 5 mmol, 1.0 M in THF) was added to a solution of 6 (829 mg, 2.00 mmol) in THF (2 mL) under Ar. The mixture was stirred at room temperature for 10 min and then cooled to −78° C. A solution of 13 (459 mg, 2.00 mmol) in THF (2 mL) was added over 1 min. The solution was maintained at −78° C. for 10 min, and then the cooling bath was removed. After 30 min, the reaction was quenched with saturated aqueous NH$_4$Cl. The mixture was allowed to warm to room temperature, poured into CH$_2$Cl$_2$, washed with water and then dried (Na$_2$SO$_4$). Column chromatography (silica, CH$_2$Cl$_2$/ethyl acetate (3:1)] afforded a pale yellow solid (512 mg, 48%): mp 97-99° C.; $^1$H NMR δ 1.44 (s, 18H), 2.42 (s, 3H), 5.59 (s, 1H), 5.93-5.98 (m, 1H), 6.01-6.07 (m, 1H), 6.12-6.16 (m, 1H), 6.65-6.69 (m, 1H), 6.78-6.82 (m, 1H), 7.20-7.28 (m, 4H), 7.64-7.74 (m, 4H), 8.68 (br s, 1H), 9.97 (br s, 1H); $^{13}$C NMR δ 21.6, 30.39, 30.43, 44.0, 82.3, 82.4, 107.7, 108.0, 110.9, 118.1, 121.2, 127.9, 128.1, 129.0, 129.1, 130.6, 130.8, 131.2, 131.6, 131.7, 133.2, 135.6, 141.6, 142.4, 144.58, 144.61, 184.8; $^{31}$P NMR δ 10.30; Anal. Calcd for $C_{31}H_{37}N_2O_4P$: C, 69.91; H, 7.00; N, 5.26. Found: C, 69.91; H, 7.11; N, 5.15.

5-[4-(Di-tert-butyloxyphosphoryl)phenyl]-1-[4-[2-(trimethylsilyl)ethynyl]benzoyl]dipyrromethane (16). Following the procedure described for compound 15, reaction of 6 (829 mg, 2.00 mmol) and 14 (623 mg, 2.00 mmol) followed by column chromatography [silica, $CH_2Cl_2$/ethyl acetate (3:1)] afforded a pale yellow solid (853 mg, 69%): mp 116-117° C.; $^1H$ NMR δ 0.26 (s, 9H), 1.45 (s, 18H), 5.58 (s, 1H), 5.93-5.99 (m, 1H), 6.03-6.09 (m, 1H), 6.12-6.18 (m, 1H), 6.70 (s, 1H), 6.73-6.80 (m, 1H), 7.19-7.27 (m, 2H), 7.53 (d, J=8.0 Hz, 2H), 7.65-7.78 (m, 4H), 8.45 (br s, 1H), 9.82 (br s, 1H); $^{13}C$ NMR δ −0.12, 30.43, 30.46, 44.0, 82.3, 82.42, 82.45, 82.49, 82.53, 97.3, 104.2, 107.8, 108.1, 111.2, 118.2, 121.5, 126.6, 127.9, 128.1, 128.8, 130.4, 130.6, 131.3, 131.6, 131.7, 131.8, 133.3, 137.9, 142.1, 144.49, 144.53, 183.9; $^{31}P$ NMR δ 10.26; Anal. Calcd for $C_{35}H_{43}N_2O_4PSi$: C, 68.38; H, 7.05; N, 4.56. Found: C, 68.51; H, 7.12; N, 4.51.

5,15-Bis[4-(di-tert-butyloxyphosphoryl)phenyl]-10,20-di-p-tolylporphyrin (17). A solution of 15 (266 mg, 0.500 mmol) in THF/methanol [9 mL, (3:1)] was treated with $NaBH_4$ (475 mg, 12.5 mmol). The resulting carbinol (15-OH) was dissolved in $CH_3CN$ (100 mL) and treated with TFA (230 μL, 3.0 mmol, 30 mM). After 5 min, a sample of DDQ (170 mg, 0.75 mmol) was added. After 1 h, TEA (420 μL, 3.0 mmol) was added. The mixture was concentrated and chromatographed [silica, $CH_2Cl_2$/ethyl acetate (3:1)], affording a purple solid (72 mg, 28%): $^1H$ NMR δ −2.78 (br s, 2H), 1.68 (s, 36H), 2.71 (s, 6H), 7.56 (d, J=8.0 Hz, 4H), 8.10 (d, J=8.0 Hz, 4H), 8.16-8.23 (m, 4H), 8.26-8.33 (m, 4H), 8.80 (d, J=4.8 Hz, 4H), 8.91 (d, J=4.8 Hz, 4H); $^{31}P$ NMR δ 10.41; LDMS obsd 1027.6, 972.5 [(M−tert-Bu)$^+$], 915.9 [(M−2×tert-Bu)$^+$], 860.3 [(M−3×tert-Bu)$^+$], 802.8 [(M−4×tert-Bu)$^+$]; FABMS obsd 1026.4604; calcd 1026.4614 ($C_{62}H_{68}N_4O_6P_2$); $\lambda_{abs}$ (THF) 418, 514, 548, 592, 647 nm.

1-Bromo-5-[4-(di-tert-butyloxyphosphoryl)phenyl]-9-p-toluoyldipyrromethane (18). A solution of 15 (266 mg, 0.500 mmol) in THF (10 mL) was cooled to −78° C. under Ar. A sample of NBS (89 mg, 0.50 mmol) was added and the reaction mixture was stirred for 1 h at −78° C. Hexanes (10 mL) and water (10 mL) were added and the mixture was allowed to warm to room temperature. The organic phase was extracted with $CH_2Cl_2$, dried ($Na_2SO_4$) and concentrated under reduced pressure without heating. Column chromatography [silica, $CH_2Cl_2$/ethyl acetate (3:1)] afforded a pale brown powder (239 mg, 78%): mp 132-134° C. (dec.); NMR δ 1.44 (s, 18H), 2.42 (s, 3H), 5.55 (s, 1H), 5.85-5.90 (m, 1H), 6.00-6.06 (m, 1H), 6.07-6.09 (m, 1H), 6.70-6.81 (m, 1H), 7.10-7.26 (m, 4H), 7.60-7.70 (m, 4H), 9.20 (br s, 1H), 10.38 (br, 1H); $^{13}C$ NMR δ 30.66, 30.70, 44.3, 82.7, 82.8, 98.4, 109.9, 110.3, 111.4, 121.6, 128.1, 128.2, 129.2, 129.5, 131.2, 131.6, 131.9, 132.0, 132.3, 133.6, 135.7, 141.2, 142.7, 144.2, 144.3, 185.3; $^{31}P$ NMR δ 9.99; Anal. Calcd for $C_{31}H_{36}BrN_2O_4P$: C, 60.89; H, 5.93; N, 4.58. Found: C, 59.93; H, 6.07; N, 4.10.

Zn(II)-10-[4-(Di-tert-butyloxyphosphoryl)phenyl]-17,18-dihydro-18,18-dimethyl-5-p-tolylporphyrin (Zn20). A solution of 18 (183 mg, 0.300 mmol) in THF/methanol [12.5 mL (4:1)] was treated with $NaBH_4$ (114 mg, 3.00 mmol). After 15 min, the reaction mixture was quenched with cold water and extracted with $CH_2Cl_2$. The organic layer was dried ($K_2CO_3$) and concentrated under reduced pressure without heating to afford mono-carbinol 18-OH as a foam. The latter was dissolved in $CH_3CN$ (3 mL) and 19 (57 mg, 0.30 mmol) was added followed by TFA (23 μL, 0.30 mmol). The reaction mixture was stirred at room temperature for 30 min, and then diluted with 27 mL of $CH_3CN$. Samples of AgOTf (231 mg, 0.900 mmol), $Zn(OAc)_2$ (826 mg, 4.50 mmol), and 2,2,6,6-tetramethylpiperidine (2.4 mL, 9.0 mmol) were added. The resulting mixture was refluxed for 18 h exposed to air. The mixture was concentrated. Column chromatography [silica, $CH_2Cl_2$/ethyl acetate (3:1)] afforded a purple-green solid (39 mg, 17%): $^1H$ NMR (THF-$d_8$) δ 1.57 (s, 18H), 2.04 (s, 6H), 2.65 (s, 3H), 4.53 (s, 2H), 7.49 (d, J=7.6 Hz, 2H), 7.93 (d, J=7.6 Hz, 2H), 7.96-8.02 (m, 2H), 8.07-8.14 (m, 2H), 8.23 (d, J=4.4 Hz, 1H), 8.31 (d, J=4.4 Hz, 1H), 8.50 (d, J=4.4 Hz, 1H), 8.55-8.65 (m, 5H); $^{31}P$ NMR δ 14.32; LDMS obsd 763.2, 700.1 [(M−tert-Bu)$^+$], 648.8 [(M−2×tert-Bu)$^+$], 586.6 [[M−(2×tert-Bu)−Zn]$^+$]; FABMS obsd 760.2548; calcd 760.2521 ($C_{43}H_{45}N_4O_3PZn$); $\lambda_{abs}$ (THF) 412, 607 nm.

Zn(II)-17,18-Dihydro-10-[4-(dihydroxyphosphoryl)phenyl]-18,18-dimethyl-5-p-tolylporphyrin (Zn21). A solution of Zn20 (20.0 mg, 26.0 μmol) in $CHCl_3$ (5 mL) was treated with TEA (0.073 mL, 0.52 mmol) and TMS—Cl (0.049 mL, 0.39 mmol). The cloudy mixture was stirred at reflux for 4 h, at which time TLC indicated the absence of starting material [$R_f$ for Zn20=1, $R_f$ for Zn21=0.1 ($CHCl_3$/MeOH, 1:1)]. Water was added and the organic phase was extracted with $CHCl_3$, dried ($Na_2SO_4$) and concentrated. Trituration with hexanes afforded a purple solid (15 mg, 88%): The acquisition of $^1H$ and $^{31}P$ NMR in $CDCl_3$, THF-$d_8$, $CD_3OD$, or DMSO-$d_6$ did not show any clear indication of peaks; MALDI-MS (POPOP) obsd 648.5, calcd 648.1 ($C_{35}H_{29}N_4O_3PZn$); $\lambda_{abs}$ (THF) 414, 608 nm. A FABMS spectrum gave very weak, uninformative signals.

Zn(II)-5-[4-(Di-tert-butyloxyphosphoryl)phenyl]-10,20-dimesityl-15-[4-[2-(trimethylsilyl)ethynyl]phenyl]porphyrin (Zn23). Samples of Zn(II)-5-(4-iodophenyl)-10,20-dimesityl-15-[4-[2-(trimethylsilyl)ethynyl]phenyl]porphyrin (191 mg, 194 μmol) and di-tert-butylphosphite (388 μmol, 1.94 mmol) were coupled using [Pd(PPh$_3$)$_4$] (22 mg, 19 mmol) in toluene/TEA [6 mL, (5:1)] at 80° C. under argon for 16 h. Column chromatography [silica, $CHCl_3$→$CHCl_3$/MeOH (10:1); silica, $CHCl_3$/MeOH (4:1)] followed by trituration with hexanes afforded a purple solid (94 mg, 46%): $^1H$ NMR (THF-$d_8$) δ 0.36 (s, 9H), 1.63 (s, 18H), 1.84 (s, 12H), 2.61 (s, 6H), 7.30 (s, 4H), 7.81 (d, J=8.0 Hz, 2H), 8.11-8.14 (m, 2H), 8.18 (d, J=8.0 Hz, 2H), 8.24-8.27 (m, 2H), 8.66-8.68 (m, 4H), 8.75-8.78 (m, 4H); LDMS obsd 1050.5, 996.6 [(M−tert-Bu)$^+$], 935.6 [(M−2×tert-Bu)$^+$]; FABMS obsd 1048.3855; calcd 1048.3867 ($C_{63}H_{65}N_4O_3PSiZn$); $\lambda_{abs}$ 424, 483, 514, 550, 590 nm; $\lambda_{em}$ ($\lambda_{ex}$=550 nm) 597, 646 nm.

Dyad-1. Samples of Zn9 (49 mg, 0.050 mmol) and Zn22 (47 mg, 0.050 mmol) were treated with Pd$_2$(dba)$_3$ (6.9 mg, 7.5 μmol) and P(o-tol)$_3$ (18 mg, 0.06 mmol) in toluene/TEA [18 mL, (5:1)] at 35° C. under argon. After 4 h, an identical batch of catalyst was added. The reaction was continued for another 7 h. Purification by a silica column [$CHCl_3$/MeOH (98:2)], a preparative SEC column (THF), and a short silica column [$CHCl_3$/MeOH (98:2)] afforded a brown-purple solid (48 mg, 54%): $^1H$ NMR (THF-$d_8$) δ 1.65 (s, 18H), 1.85-1.91 (m, 30H), 2.59-2.65 (m, 15H), 7.28-7.34 (m, 10H), 8.03-8.08 (m, 4H), 8.12-8.19 (m, 2H), 8.26-8.34 (m, 6H), 8.62-8.66 (m, 4H), 8.68-8.72 (m, 4H), 8.74 (d, J=4.4 Hz, 2H), 8.78 (d, J=4.4 Hz, 2H), 8.87 (d, J=4.4 Hz, 2H), 8.90 (d, J=4.4 Hz, 2H); $^{31}P$ NMR δ 11.06; MALDI-MS (POPOP) obsd 1781.2, 1723.4 [(M−tert-Bu)$^+$], 1667.0 [(M−2×tert-Bu)$^+$]; FABMS obsd 1776.6273; calcd 1776.6317 ($C_{113}H_{101}N_8O_3PZn_2$); $\lambda_{abs}$ 428, 551, 593 nm.

Dyad-2. A solution of Dyad-1 (31 mg, 0.017 mmol) and TEA (47 μL, 0.34 mmol) in $CHCl_3$ (3.4 mL) was treated with TMS—Cl (33 μL, 0.26 mmol) at 65° C. under argon for 4 h. Water was added and the organic layer was dried ($Na_2SO_4$) and concentrated. Trituration with hexanes afforded a purple solid (23 mg, 82%): $^1H$ NMR ($CD_3OD$) δ 1.82-1.92 (m, 30H), 2.57-2.65 (m, 15H), 7.25-7.34 (m, 10H), 7.98-8.06 (m, 4H), 8.18-8.23 (m, 4H), 8.26-8.32 (m, 4H), 8.58-8.72 (m, 10H), 8.78-8.88 (m, 6H); $^{31}P$ NMR δ (not observed); MALDI-MS (POPOP) obsd 1667.4; FABMS obsd 1664.5020; calcd 1664.5065 ($C_{105}H_{85}N_8O_3PZn_2$); $\lambda_{abs}$ 428, 551, 591 nm.

5-[4-(Diethoxyphosphorylmethyl)phenyl]-10,15,20-trimesitylporphyrin (24) (Method A). A solution of 26 (200 mg, 240 μmol) in triethylphosphite (2.1 mL) and toluene (8 mL) was heated to 120° C. under argon for 24 h. The reaction mixture was cooled and concentrated under vacuum (to remove excess triethylphosphite; bp=154° C.). Column chromatography [silica, $CHCl_3 \rightarrow CHCl_3$/ethyl acetate (95:5)] afforded a purple solid (165 mg, 80%). Characterization data were consistent with those described above.

(Method B). A solution of diethylphosphite (1.16 mL, 9.00 mmol) in THF (20 mL) was treated with NaH (206 mg, 8.60 mmol) and the mixture was stirred at room temperature under argon for 1 h. A 1.9 mL aliquot of this solution (864 mmol, 3 eq) was then added to a solution of 26 (240 mg, 288 μmol) in THF (20 mL). The reaction mixture was stirred at under argon for 24 h. Water and $CH_2Cl_2$ were added. The layers were separated and the aqueous layer was washed with $CH_2Cl_2$. The organic layers were combined, dried ($K_2CO_3$), and concentrated. Column chromatography [silica, $CHCl_3 \rightarrow CHCl_3$/ethyl acetate (95:5)] afforded a purple solid (187 mg, 73%). Characterization data were consistent with those described above.

Zn(II)-5-[4-(Diethoxyphosphorylmethyl)phenyl]-10,15,20-trimesitylporphyrin (Zn24). A solution of 24 (163 mg, 189 μmol) in $CHCl_3$ (15 mL) was treated with a solution of $Zn(OAc)_2 \cdot 2H_2O$ (207 mg, 943 μmol) in methanol (3 mL). Column chromatography [silica, $CHCl_3$/ethyl acetate (95:5)] afforded a purple solid (164 mg, 94%): $^1H$ NMR (THF-$d_8$) δ 1.35 (t, J=6.9 Hz, 6H), 1.86 (s, 18H), 2.61 (s, 9H), 3.46 (d, J=22.0 Hz, 2H), 4.14 (p, J=7.2 Hz, 4H), 7.29 (s, 6H), 7.70 (dd, $J^1$=7.5 Hz, $J^2$=1.8 Hz, 2H), 8.11 (d, J=7.5 Hz, 2H), 8.62-8.63 (m, 6H), 8.76 (d, J=4.5 Hz, 2H); $^{31}P$ NMR δ 26.8; LDMS obsd 956.0; FABMS obsd 952.3466; calcd 952.3460 ($C_{58}H_{57}N_4O_3PZn$); $\lambda_{abs}$=425, 555, 595 nm.

Co(II)-5-[4-(Diethoxyphosphorylmethyl)phenyl]-10,15,20-trimesitylporphyrin (Co24). A solution of 24 (184 mg, 206 μmol) in $CHCl_3$ (100 mL) was treated with a suspension of $Co(OAc)_2$ (365 mg, 2.06 mmol) in methanol (20 mL). The mixture was heated to reflux under argon. After 12 h, the mixture was cooled and washed with water. The organic layer was dried ($K_2CO_3$), filtered, and concentrated. Column chromatography [silica, $CHCl_3$/ethyl acetate (9:1)] afforded a red solid (133 mg, 68%): $^1H$ NMR δ 2.23 (t, J=6.3 Hz, 6H), 3.28 (br s, 6H), 3.58 (br s, 12H), 3.93 (s, 3H), 4.01 (s, 6H), 4.81 (d, J=21.6 Hz, 2H), 5.12 (m, 4H), 9.17 (s, 2H), 9.30 (s, 4H), 9.66 (s, 2H), 12.49 (br s, 2H), 15.25 (br s, 4H), 15.50 (br s, 4H); LDMS obsd 948.9. FABMS obsd 947.3525, calcd 947.3500 ($C_{58}H_{57}CoN_4O_3P$); $\lambda_{abs}$=412, 528 nm.

Co(II)-5-[4-(Dihydroxyphosphorylmethyl)phenyl]-10,15,20-trimesitylporphyrin (Co25). A solution of Co24 (126 mg, 133 μmol) in $CHCl_3$ (13 mL) was treated with samples of TEA (371 μL, 2.66 mmol) and TMS—Br (263 μL, 2.00 mmol) at reflux under argon for 4 h. The mixture was cooled and then washed with water. The organic layer was dried ($Na_2CO_3$), filtered and concentrated. The resulting red solid was washed with hexanes to afford a red solid (110 mg, 92%): $^1H$ NMR analysis was not successful due both to aggregation and the paramagnetic Co(II). LDMS obsd 891.1; FABMS obsd 891.2883, calcd 891.2874 ($C_{54}H_{49}CoN_4O_3P$); $\lambda_{abs}$=413, 529 nm.

Zn(II)-5-[4-(Dihydroxyphosphorylmethyl)phenyl]-10,15,20-trimesitylporphyrin (Zn25; from Zn24). A mixture of Zn24 (178 mg, 186 μmol) in $CHCl_3$ (18 mL) and TEA (518 μL, 3.72 mmol) was heated to reflux, affording a homogeneous solution. A sample of TMS—Br (369 μL, 2.80 mmol) was then added. The solution was stirred at reflux for 4 h, then cooled. The reaction mixture was washed with water. The organic layer was collected, dried ($Na_2SO_4$), and concentrated. Column chromatography [silica, $CHCl_3$/MeOH (1:1)] afforded a purple solid. The solid was washed with hexanes, then water, then hexanes again to afford a purple solid (130 mg, 78%): $^1H$ NMR (DMSO-$d_6$) δ 1.71 (s, 9H), 1.76 (s, 9H), 2.54 (s, 3H), the other methyl signal is presumed to be buried under the DMSO solvent peak, 7.20 (s, 3H), 7.36 (s, 3H), 7.69 (d, 2H), 7.97 (d, 2H), 8.47 (s, 6H), 8.74 (s, 2H); $^{31}P$ NMR analysis was attempted but no peak could be observed; LDMS obsd 927.7 [(M+OMe)$^+$]; FABMS obsd 896.2870; calcd 896.2834 ($C_{48}H_{49}N_4O_3PZn$); $\lambda_{abs}$=426, 556, 596 nm; $\lambda_{em}$ ($\lambda_{ex}$=556 nm) 601, 655 nm.

Zn(II)-5-[4-(Dihydroxyphosphorylmethyl)phenyl]-10,15,20-trimesitylporphyrin (Zn25; from Zn27). A mixture of Zn27 (159 mg, 172 μmol) in $CHCl_3$ (17 mL) and TEA (479 μL, 3.44 mmol) was heated to reflux, affording a homogeneous solution. A sample of TMS—Br (341 μL, 2.58 mmol) was then added. The solution was stirred at reflux for 2 h then cooled. Analogous workup as described above yielded a purple solid (120 mg, 77%). Characterization data were consistent with those described above.

5-[4-(Bromomethyl)phenyl]-10,15,20-trimesitylporphyrin (26). Samples of 4-bromomethylbenzaldehyde (700 mg, 3.52 mmol), mesitaldehyde (1.56 mL, 10.6 mmol), and pyrrole (977 μL, 14.1 mmol) were condensed in $CHCl_3$ (193 mL) in the presence of $BF_3 \cdot O(Et)_2$ (435 μL, 3.43 mmol) at room temperature for 1 h. DDQ (2.41 g, 10.6 mmol) was added. After 1 h, TEA (478 μmol, 3.43 mmol) was added and the crude mixture was passed over a pad of silica [$CH_2Cl_2$/hexanes (1:1)] followed by column chromatography [silica, hexanes/$CH_2Cl_2$ (7:3), 10×30 cm] to afford a purple solid (465 mg, 16%): $^1H$ NMR δ −2.57 (br s, 2H), 1.86 (s, 18H), 2.63 (s, 9H), 4.85 (s, 2H), 7.28 (s, 6H), 7.77 (d, J=7.2 Hz, 2H), 8.18 (d, J=7.2 Hz, 2H), 8.64 (s, 4H), 8.68 (d, J=4.4 Hz, 2H), 8.77 (d, J=4.4 Hz, 2H); LDMS obsd 830.4, 751.5 [(M−Br)$^+$]. FABMS obsd 832.3135; calcd 832.3141 ($C_{54}H_{49}BrN_4$); $\lambda_{abs}$=420, 515, 547, 592, 649 nm; $\lambda_{em}$ ($\lambda_{ex}$=515 nm) 650, 720 nm.

5-[4-(Dimethoxyphosphorylmethyl)phenyl]-10,15,20-trimesitylporphyrin (27). A solution of 26 (200 mg, 240 μmol) in trimethylphosphite (2.2 mL) and toluene (5 mL) was heated to 120° C. under argon for 17 h. The reaction mixture was cooled and concentrated under vacuum. The residue was chromatographed [silica, $CHCl_3 \rightarrow CHCl_3$/ethyl acetate (95:5)] to afford a purple solid (164 mg, 79%): $^1H$ NMR δ −2.57 (br s, 2H), 1.84-1.85 (m, 18H), 2.62 (s, 9H), 3.50 (d, J=21.6 Hz, 2H), 3.87 (d, J=11.1 Hz, 6H), 7.27 (s, 6H), 7.67 (dd, $J^1$=8.4 Hz, $J^2$=1.8 Hz, 2H), 8.15 (d, J=7.8 Hz, 2H), 8.63 (s, 4H), 8.67 (d, J=4.8 Hz, 2H), 8.75 (d, J=4.8 Hz, 2H); $^{31}P$ NMR δ 29.50; LDMS obsd 863.2; FABMS obsd 862.4045; calcd 862.4012 ($C_{56}H_{55}N_4O_3P$); $\lambda_{abs}$=421, 514, 547, 593, 649 nm.

Zn(II)-5-[4-(Dimethoxyphosphorylmethyl)phenyl]-10,15,20-trimesitylporphyrin (Zn27). A solution of 27 (160 mg, 185 μmol) in $CHCl_3$ (12 mL) was treated with a solution of $Zn(OAc)_2 \cdot 2H_2O$ (204 mg, 0.929 mmol) in methanol (3 mL). Column chromatography [silica, $CHCl_3$/ethyl acetate (95:5)] afforded a purple solid (169 mg, 98%): $^1H$ NMR (THF-$d_8$) δ 1.85 (s, 18H), 2.60 (s, 9H), 3.47 (d, J=22.0 Hz, 2H), 3.77 (d, J=11.1 Hz, 6H), 7.28 (s, 6H), 7.69 (d, J=7.5 Hz, 2H), 8.11 (d, J=7.6 Hz, 2H), 8.61-8.63 (m, 6H), 8.75 (d, J=4.5 Hz, 2H); $^{31}P$ NMR δ 29.2; LDMS obsd 926.1; FABMS obsd 924.3146; calcd 924.3147 ($C_{56}H_{53}N_4O_3PZn$); $\lambda_{abs}$=423, 551, 592 nm.

4-(Diethoxyphosphorylmethyl)benzaldehyde (28). Triethylphosphite (9.28 mL, 53.3 mmol) and α-bromo-p-toluic acid (10.4 g, 48.4 mmol) were suspended in toluene (25 mL) and the mixture was heated to reflux for 18 h. The mixture was cooled to room temperature. After 12 h, the resulting white solid was collected by suction filtration, washed with petroleum ether and dried to yield 4-(diethoxyphosphorylmethyl)benzoic acid as a white solid (10.2 g, 77%): mp 117-120° C.; $^1H$ NMR δ 1.26 (t, J=6.8 Hz, 6H), 3.24 (d, J=25.6 Hz, 2H), 4.06 (m, 4H), 7.38-7.40 (m, 2H), 8.02 (d, J=7.6 Hz, 2H), 11.4 (br s, 1H); $^{13}C$ NMR δ 16.5, 16.6, 33.4, 34.8, 62.8, 62.9, 129.1, 129.2, 130.00, 130.05, 130.10, 130.48, 130.51, 137.3, 137.4, 170.1; FABMS obsd 273.0896, calcd 273.0892; Anal. Calcd. for $C_{12}H_{17}O_5P$: C, 52.94; H, 6.29. Found: C, 52.92; H, 6.28. A suspension of 4-(diethoxyphosphorylmethyl)benzoic acid (9.99 g, 36.7 mmol) in anhydrous THF (40 mL) at 0° C. was treated dropwise over 10 min with borane-THF complex (40.3 mL, 40.3 mmol, 1.0 M in THF). The reaction mixture was stirred at room temperature for 4 h. The reaction was quenched by slow addition of water. The mixture was concentrated and the residue was partitioned between water (100 mL) and $CH_2Cl_2$ (100 mL). The aqueous layer was washed with $CH_2Cl_2$. The combined organic layers were washed with water, dried ($MgSO_4$), and concentrated to give a yellow oil. Analysis by TLC and $^1H$ NMR spectroscopy showed starting material (~10%) and the desired benzyl alcohol. The latter (9.56 g) was dissolved in $CH_2Cl_2$ and rapidly added to a sample of PCC (10.8 g, 50.1 mmol) in $CH_2Cl_2$ (50 mL) with rapid stirring. After 2 h, ethyl ether (150 mL) was added and the organic solution was decanted from the tarry residue. The residue was washed with ethyl ether (3×50 mL). The combined organic solution was filtered through Florisil and concentrated to a brown oil. Kugelrohr distillation (190° C. @ 0.05 Ton) afforded a clear, colorless oil (6.54 g, 77%): $^1H$ NMR δ 1.24 (t, J=7.2 Hz, 6H), 3.21 (d, J=22.4 Hz, 2H), 4.03 (m, 4H), 7.45-7.48 (m, 2H), 7.83 (d, J=7.6 Hz, 2H), 9.99 (s, 1H); $^{13}C$ NMR δ 16.1, 16.2, 33.0, 34.9, 62.1, 62.2, 77.2, 129.49, 129.53, 129.6, 129.66, 129.71, 130.2, 130.2, 138.8, 138.9, 191.61, 191.63; $^{31}P$ NMR δ 25.4, 25.9; FABMS obsd 257.0949, calcd 257.0943 ($C_{12}H_{17}PO_4$).

5-[4-(Diethoxyphosphorylmethyl)phenyl]dipyrromethane (29). A solution of 28 (2.00 g, 7.81 mmol) in pyrrole (22.0 mL, 315 mmol) was treated with TFA (60 μL, 780 μmol) at room temperature under argon for 5 min. TEA (109 μL, 782 μmol) was added and the reaction mixture was concentrated under vacuum. Column chromatography (silica, ethyl acetate) afforded a viscous, yellow oil (1.33 g, 46%): $^1H$ NMR ($CD_2Cl_2$) δ 1.25 (t, J=6.4 Hz, 6H), 3.11 (d, J=21.6 Hz, 2H), 4.01 (m, 4H), 5.43 (s, 1H), 5.86 (s, 2H), 6.11 (d, J=2.8 Hz, 2H), 6.67 (s, 2H), 7.14 (d, J=8.0 Hz, 2H), 7.23 (d, J=8.0 Hz, 2H), 8.29 (br s, 2H); $^{13}C$ NMR δ 16.6, 16.7, 32.5, 34.3, 43.74, 43.75, 62.35, 62.44, 107.3, 108.3, 117.5, 128.8, 128.9, 130.06, 130.14, 130.2, 132.81, 132.83, 141.39, 141.44; $^{31}P$ NMR δ 27.6; FABMS obsd 372.1598, calcd 372.1603 ($C_{20}H_{25}N_2O_3P$).

5-[4-(Diethoxyphosphorylmethyl)phenyl]-10,15,20-tri-p-tolylporphyrin (31). A solution of 30 (360 mg, 762 μmol) in dry THF/methanol [44 mL, (10:1)] was treated with $NaBH_4$ (576 mg, 15.2 mmol). After 40 min, the reaction mixture was poured into a stirred mixture of saturated aqueous $NH_4Cl$ (150 mL) and $CH_2Cl_2$ (150 mL). The organic phase was washed with water and brine, dried ($Na_2SO_4$), and concentrated. The resulting 30-diol was dissolved in $CH_2Cl_2$ (305 mL). The solution was treated with 29 (284 mg, 762 μmol) and $InCl_3$ (22 mg, 99 μmol) under argon for 1 h. DDQ (519 mg, 2.29 mmol) was added and the mixture was stirred for 1 h at room temperature. TEA (1 mL) was added and the reaction mixture was chromatographed [silica, $CHCl_3$/ethyl acetate (9:1); silica, $CHCl_3$/ethyl acetate (95:5)] to afford a purple solid. The solid was dissolved in $CHCl_3$ (120 mL) and treated overnight with a solution of $Zn(OAc)_2 \cdot 2H_2O$ (220 mg, 1.00 mmol) in methanol (12 mL) at room temperature. The reaction mixture was concentrated and chromatographed [silica, $CHCl_3$/ethyl acetate (4:1)] to afford a purple solid (95 mg). This compound could not be analyzed for purity due to its poor solubility. The solid was suspended (95 mg, 110 μmol) in $CH_2Cl_2$ (80 mL) and treated with TFA (420 μL, 5.5 mmol, 50 eq) at room temperature under argon for 1 h. The solution was washed with 10% aqueous $NaHCO_3$ and water. The organic layer was dried ($Na_2SO_4$), filtered, and concentrated. Column chromatography [silica, $CHCl_3$/ethyl acetate (1:1)] afforded a purple solid (82 mg, 12%): $^1H$ NMR δ −2.78 (br s, 2H), 1.41 (t, J=6.9 Hz, 6H), 2.71 (s, 9H), 3.50 (d, J=21.6 Hz, 2H), 4.22 (p, J=6.9 Hz, 4H), 7.55 (d, J=7.8 Hz, 6H), 7.69 (d, J=7.2 Hz, 2H), 8.10 (d, J=7.8 Hz, 6H), 8.16 (d, J=7.2 Hz, 2H), 8.80-8.86 (m, 8H); $^{31}P$ NMR δ 27.1; LDMS obsd 805.2; FABMS obsd 806.3401, calcd 806.3386 ($C_{52}H_{47}N_4O_3P$); $\lambda_{abs}$=421, 516, 551, 593, 649 nm.

5-(6-Bromohexyl)-10,15,20-tri-p-tolylporphyrin (33). A solution of 30 (236 mg, 0.500 mmol) in dry THF/$CH_3OH$ [22 mL, (10:1)] was treated with $NaBH_4$ (378 mg, 10.0 mmol). After 40 min, the reaction mixture was poured into a stirred mixture of aqueous $NH_4Cl$ (100 mL) and $CH_2Cl_2$ (100 mL). The organic phase was isolated, washed with water, dried ($Na_2SO_4$), and concentrated. The resulting 30-diol was dissolved in $CH_2Cl_2$ (200 mL). The solution was treated with 32 (153 mg, 0.500 mmol) and $InCl_3$ (14.2 mg, 63.7 μmol) under argon for 40 min. DDQ (341 mg, 1.50 mmol) was added and the mixture was stirred at room temperature for 1 h. TEA (3 mL) was added and the mixture was concentrated and filtered [silica, hexanes/$CH_2Cl_2$ (7:3)]. The porphyrin band was collected and recrystallized ($CH_2Cl_2$/$CH_3OH$) to afford a purple solid (88 mg, 24%): $^1H$ NMR δ −2.72 (s, 2H), 1.60-1.70 (m, 2H), 1.75-1.84 (m, 2H), 1.85-1.96 (m, 2H), 2.52-2.62 (m, 2H), 2.71 (s, 3H), 2.73 (s, 6H), 3.38-3.44 (m, 2H), 5.00-5.07 (m, 2H), 7.52-7.59 (m, 6H), 8.05-8.12 (m, 6H), 8.82 (s, 4H), 8.95 (d, J=5.1 2H), 9.47 (d, J=5.1 Hz, 2H); LDMS obsd 743.8; FABMS obsd 742.2653, calcd 742.2671 ($C_{47}H_{43}BrN_4$); $\lambda_{abs}$=418, 516, 550, 594, 651 nm.

Zn(II)-5-(6-Bromohexyl)-5,10,15-tri-p-tolylporphyrin (Zn33). A solution of 33 (74.4 mg, 0.100 mmol) in THF/$CH_2Cl_2$ [20 mL, (1:1)] was treated with $Zn(OAc)_2 \cdot 2H_2O$ (109 mg, 0.500 mmol). After 1 h, the mixture was concentrated and chromatographed [silica, hexanes/toluene (1:1)] to afford a purple solid (81 mg, 85%): $^1H$ NMR δ 1.60-1.70 (m, 2H), 1.80-1.96 (m, 4H), 2.52-2.62 (m, 2H), 2.67 (s, 3H), 2.70 (s, 6H), 3.45 (t, J=6.8 Hz, 2H), 5.10-5.18 (m, 2H), 7.50-7.58 (m, 6H), 8.01-8.08 (m, 6H), 8.76-8.80 (m, 4H), 8.91 (d, J=4.8 Hz, 2H), 9.60 (d, J=4.8 Hz, 2H); LDMS obsd 806.9; FABMS obsd 804.1825, calcd 804.1806 ($C_{47}H_{41}BrN_4Zn$); $\lambda_{abs}$=424, 553, 591 nm.

Zn(II)-5-[6-(Diethoxyphosphoryl)hexyl]-10,15,20-tri-p-tolylporphyrin (Zn34). A solution of Zn33 (40.4 mg, 50.1 μmol) in triethylphosphite (2 mL) was refluxed under argon for 2 d. The mixture was chromatographed [silica, $CH_2Cl_2 \rightarrow CH_2Cl_2$/THF (95:5)] and the second red fraction was collected, affording a purple solid (42.1 mg, 100%): $^1H$ NMR δ 1.67 (t, J=7.0 Hz, 6H), 1.48-1.68 (m, 6H), 1.77-1.90 (m, 2H), 2.46-2.62 (m, 2H), 2.67 (s, 3H), 2.70 (s, 6H), 3.80-3.96 (m, 4H), 5.10-5.18 (m, 2H), 7.51-7.58 (m, 6H), 8.01-8.08 (m, 6H), 8.75-8.80 (m, 4H), 8.91 (d, J=4.8 Hz, 2H), 9.60 (d, J=4.8 Hz, 2H); $^{31}P$ NMR δ 31.9; LDMS obsd 864.9; FABMS obsd 862.3003, calcd 862.2990 ($C_{51}H_{51}N_4O_3PZn$); $\lambda_{abs}$=424, 558, 599 nm.

Zn(II)-5-[6-(Dihydroxyphosphoryl)hexyl]-10,15,20-tri-p-tolylporphyrin (Zn35). A solution of Zn34 (43.2 mg, 50.0 μmol) in $CHCl_3$ (15 mL) was treated with TEA (140 μL, 1.0 mmol) followed by TMS—Br (99.0 μL, 0.75 mmol). The mixture was stirred overnight at 60-65° C. under argon. The reaction mixture was cooled and water and $CH_2Cl_2$ were added. The organic layer was separated, washed with water, dried ($Na_2SO_4$) and concentrated. Recrystallization ($CH_2Cl_2$/hexanes) afforded a purple solid (35.4 mg, 88%): $^1H$ NMR δ 0.60-1.78 (br m, 4H), 2.16-2.36 (m, 4H), 2.40-2.50 (m, 2H), 2.62 (s, 6H), 2.64 (s, 3H), 4.98-5.05 (m, 2H), 7.45-7.51 (m, 6H), 7.98-8.03 (m, 6H), 8.75 (s, 4H), 8.83-8.87 (m, 2H), 9.49-9.53 (m, 2H); $^{31}P$ NMR δ 27.3; LDMS obsd 809.1; FABMS obsd 806.2392, calcd 806.2364 ($C_{47}H_{43}N_4O_3PZn$); $\lambda_{abs}$=424, 558, 600 nm.

1-(4-Cyanophenyl)-1,1,1-tri-p-tolylmethane (37). A mixture of 36 (21.0 g, 47.6 mmol) and CuCN (6.39 g, 71.4 mmol) in DMF (125 mL) was heated to reflux under argon for 18 h. The reaction mixture was cooled and poured into 500 mL of aqueous ammonia. Air was bubbled through the mixture for 2 h. The mixture was filtered and the resulting solid was washed with water until the washings were neutral (~1 L). The solid was dissolved in toluene and the excess water was removed in a separatory funnel. The organic layer was dried ($Na_2SO_4$), filtered, and concentrated. Column chromatography (silica, toluene, 7×25 cm) afforded a beige solid (11.1 g, 60.0%): mp 207-209° C.; $^1H$ NMR δ 2.32 (s, 9H), 7.03-7.08 (m, 12H), 7.36 (d, J=8.4 Hz, 2H), 7.52 (d, J=8.4 Hz, 2H); $^{13}C$ NMR δ 20.9, 64.2, 109.5, 119.0, 128.1, 128.2, 128.4, 128.7, 130.4, 130.7, 130.90, 130.94, 131.2, 131.6, 135.8, 143.0, 152.9;

FABMS obsd 388.2060, calcd 388.2065 (M+H); Anal. Calcd for $C_{29}H_{25}N$: C, 89.89; H, 6.50; N, 3.61. Found: C, 89.21; H, 6.60; N, 3.47.

1,1,1-Tris[4-(diethoxyphosphorylmethyl)phenyl]-1-(4-formylphenyl)methane (41). A solution of 37 (10.36 g, 26.7 mmol) in benzene (200 mL) was heated to reflux under argon. Then, samples of NBS (16.2 g, 90.9 mmol, 3.3 eq) and AIBN (149 mg, 909 μmol) were added all at once. The mixture was refluxed for 20 min then cooled. The mixture was filtered through a silica pad (7×10 cm, eluted with toluene) to remove succinimide. Removal of solvent afforded crude 1,1,1-tris[4-(bromomethyl)phenyl]-1-(4-cyanophenyl)methane (38) as an off-white solid (16.5 g). Analysis by $^1H$ NMR spectroscopy showed ~10% of tolyl resonances, indicating incomplete bromination. A solution of crude 38 (6.00 g, 9.61 mmol) in $CH_2Cl_2$/toluene [60 mL, (1:1)] at 0° C. was treated dropwise with a solution of DIBALH (12.0 mL, 12.0 mmol, 1.0 M solution in hexanes) under argon for 1 h. Then $CHCl_3$ (80 mL) and 2 N HCl (200 mL) were added and the mixture was stirred at room temperature for 1 h. The organic layer was separated, washed with water, dried ($Na_2SO_4$), filtered and concentrated. Column chromatography (silica, $CH_2Cl_2$) afforded crude 1,1,1-tris[4-(bromomethyl)phenyl]-1-(4-formylphenyl)methane (39) as a white solid (4.93 g). A solution of crude 39 (4.79 g, 7.64 mmol) in $CH_2Cl_2$/methanol [80 mL, (1:1)] was treated with a solution of $TiCl_4$ (153 μL, 153 μmol, 1.0 M in $CH_2Cl_2$) at room temperature under argon for 30 min. TEA (153 μL) was added. After 30 min, water (50 mL) was added. The organic phase was extracted with ethyl ether (2×100 mL). The organic layer was dried ($Na_2SO_4$), filtered, and concentrated to give crude 1,1,1-tris[4-(bromomethyl)phenyl]-1-[4-(1,1-dimethoxymethyl)phenyl]methane (40) as an off-white solid (4.51 g). A mixture of crude 40 (4.51 g, 6.70 mmol) in triethylphosphite (50 mL) was stirred under argon at 100° C. for 6 h. The solution was cooled and poured into 1 N HCl (250 mL). The mixture was extracted with ethyl acetate (150 mL). The layers were separated and the aqueous layer was washed with ethyl acetate (2×50 mL). The organic layers were combined, washed with 5% $NaHCO_3$ and water. The organic layer was dried ($Na_2SO_4$), filtered, and concentrated. Column chromatography [silica, ethyl acetate/methanol (9:1)→(8:2)] afforded the title compound as a pale yellow oil (2.89 g, 54%): $^1H$ NMR δ 1.21 (t, J=6.8 Hz, 18H), 3.11 (d, J=22.4 Hz, 6H), 4.00 (m, 12H), 7.10 (d, J=8.4 Hz, 6H), 7.18 (d, J=8.4 Hz, 6H), 7.36 (d, J=8.4 Hz, 2H), 7.73 (d, J=8.4 Hz, 2H), 9.98 (s, 1H); $^{13}C$ NMR δ 16.2, 16.3, 32.5, 33.8, 62.0, 62.1, 125.7, 128.9, 129.0, 129.1, 129.2, 129.6, 129.7, 130.8, 130.9, 131.0, 131.1, 131.4, 134.1, 144.4, 153.6, 191.8; $^{31}P$ NMR δ 27.0; FABMS obsd 799.2968, calcd 799.2930 (M+H) ($C_{41}H_{53}O_{10}P_3$).

5-[4-[1,1,1-Tris[4-(diethoxyphosphorylmethyl)phenyl]methyl]phenyl]dipyrromethane (42). A solution of 41 (2.83 g, 3.54 mmol) in pyrrole (24.7 mL, 354 mmol) was degassed with argon for 10 min. A sample of $InCl_3$ (78 mg, 0.354 mmol) was added and the mixture was stirred at room temperature for 90 min. Powdered NaOH (425 mg) was added and the mixture was stirred for 30 min. The mixture was filtered and the pyrrole was removed under vacuum. Column chromatography [silica, ethyl acetate/MeOH (3:1)] afforded a pale yellow foam (2.50 g, 77%): mp 58-61° C.; $^1$-NMR δ 1.21 (t, J=6.8 Hz, 18H), 3.10 (d, J=21.6 Hz, 6H), 3.99 (m, 12H), 5.44, (s, 1H), 5.89 (br s, 2H), 6.13 (m, 2H), 6.67 (m, 2H), 7.06-7.17 (m, 16H), 8.10 (br s, 2H); $^{13}C$ NMR δ 16.1, 16.2, 32.3, 33.7, 43.2, 62.0, 62.1, 63.7, 106.9, 107.9, 117.1, 127.3, 128.77, 128.84, 128.9, 129.0, 130.8, 130.95, 130.98, 132.4, 140.0, 144.8, 145.1, 145.2; $^{31}P$ NMR δ 27.1; FABMS obsd 915.3679, calcd 915.3668 (M+H); Anal. Calcd for $C_{49}H_{61}N_2O_9P_3$: C, 64.32; H, 6.72; O, 15.74. Found: C, 63.99; H, 6.64; O, 15.55.

5-(4-Ethynylphenyl)-1,9-bis(4-methylbenzoyl)dipyrromethane (43). A solution of 5-[4-(2-trimethylsilyl)ethynylphenyl)-1,9-bis(4-methylbenzoyl)dipyrromethane (2.00 g, 3.61 mmol) in $CHCl_3$ (75 mL) was treated with TBAF (4.33 mL, 4.33 mmol, 1.0 M in THF) at room temperature under argon for 1 h. The solution was then washed with 10% aqueous $NaHCO_3$ and water. The organic phase was dried ($Na_2SO_4$), filtered and concentrated. Column chromatography [silica, $CH_2Cl_2$/ethyl acetate (95:5)] afforded an orange foam (1.37 g, 79%): mp 122-126° C.; $^1H$ NMR δ 2.39 (s, 6H), 3.10 (s, 1H), 5.67 (s, 1H), 5.92 (m, 2H), 6.51 (m, 2H), 7.19 (d, J=8.0 Hz, 4H), 7.53 (s, 4H), 7.66 (d, J=8.0 Hz, 4H), 11.64 (brs, 2H); $^{13}C$ NMR δ 21.5, 44.9, 77.3, 83.5, 111.2, 120.6, 121.0, 128.6, 128.9, 129.8, 131.2, 132.5, 135.4, 140.3, 141.4, 142.2, 184.3; FABMS obsd 483.2059, calcd 483.2073 [M+H]; Anal. Calcd for $C_{33}H_{26}N_2O_2$: C, 82.13; H, 5.43. Found: C, 81.54; H, 5.54.

Zn(II)-5-[4-[1,1,1-Tris[4-(diethoxyphosphorylmethyl)phenyl]methyl]phenyl]-10,15,20-tri-p-tolylporphyrin (Zn44). A solution of 30 (120 mg, 250 μmol) in dry THF/methanol [11 mL, (10:1)] was treated with $NaBH_4$ (190 mg, 5.10 mmol). After 40 min, the reaction mixture was poured into a stirred mixture of saturated aqueous $NH_4Cl$ (150 mL) and $CH_2Cl_2$ (50 mL). The organic phase was washed with water and brine, dried ($Na_2SO_4$), and concentrated. The resulting 30-diol was dissolved in $CH_2Cl_2$ (100 mL) and treated with 42 (225 mg, 250 μmol) and $InCl_3$ (7.0 mg, 33 μmol) under argon for 1 h at room temperature. DDQ (170 mg, 750 μmol) was added. After 1 h, TEA (400 μL) was added. Column chromatography [silica, ethyl acetate/methanol (9:1)] afforded a purple solid (60 mg). The solid (60 mg, 0.045 mmol) was dissolved in $CHCl_3$ (30 mL) and treated overnight with a solution of $Zn(OAc)_2 \cdot 2H_2O$ (60 mg, 0.27 mmol) in methanol (5 mL). Column chromatography [silica, ethyl acetate/methanol, (9:1)] afforded a purple solid (40 mg, 63%): $^1H$ NMR (THF-$d_8$) δ 1.15-1.18 (m, 18H), 2.68-2.69 (m, 9H), 3.10 (s, 3H), 3.16 (s, 3H), 3.90-3.94 (m, 12H), 7.32-7.34 (m, 6H), 7.41-7.43 (m, 6H), 7.54-7.59 (m, 8H), 8.05-8.09 (m, 8H), 8.83-8.89 (m, 8H); $^{31}P$ NMR δ 26.71; LDMS obsd 1413.85; FABMS obsd 1410.4476, calcd 1410.4508; ($C_{81}H_{81}N_4O_9P_3Zn$); $\lambda_{abs}$=427, 558, 598 nm.

Zn(II)-5-[4-[1,1,1-Tris[4-(diethoxyphosphorylmethyl)phenyl]methyl]phenyl-15-(4-ethynylphenyl)-10,20-di-p-tolylporphyrin (Zn45). A solution of 43 (500 mg, 1.04 mmol) in THF/MeOH [38 mL, (10:1)] was treated with $NaBH_4$ (784 mg, 20.7 mmol). After 40 min, the reaction mixture was poured into a mixture of saturated aqueous $NH_4Cl$ (100 mL) and $CH_2Cl_2$ (100 mL). The organic phase was collected, dried ($Na_2SO_4$), and concentrated to a yellow foam. The resulting 43-diol was dissolved in $CH_2Cl_2$ (414 mL) and samples of 42 (950 mg, 1.04 mmol) and $Yb(OTf)_3$ (822 mg, 1.33 mmol) were added. After 25 min, DDQ (705 mg, 3.12 mmol) was added followed by TEA (1 mL). After 30 min, the reaction mixture was chromatographed [silica, ethyl acetate/MeOH (8:2)] to recover the partially purified free base porphyrin. The solid was dissolved in $CHCl_3$ (60 mL) and treated with a solution of $Zn(OAc)_2 \cdot 2H_2O$ (228 mg, 1.04 mmol) in methanol (10 mL) for 12 h. Column chromatography [silica, ethyl acetate/MeOH (9:1)→(8:2); silica, $CHCl_3$/MeOH (5:1)] afforded a purple solid (335 mg, 24%): $^1H$ NMR δ 1.16 (t, J=7.2 Hz, 18H), 2.69 (s, 6H), 3.12 (d, J=21.6 Hz, 6H), 3.77 (s, 1H), 3.90 (m, 12H), 7.30-7.33 (m, 6H), 7.41 (d, J=8.0 Hz, 6H), 7.55-7.59 (m, 6H), 7.85 (d, J=8.0 Hz, 2H), 8.06-8.10 (m, 6H), 8.17 (d, J=8.0 Hz, 2H), 8.81 (d, J=4.4 Hz, 2H), 8.86-8.90 (m, 6H); $^{31}P$ NMR δ 26.6; MALDI-MS (POPOP) 1424.9; FABMS obsd 1420.4305, calcd 1420.4351 ($C_{82}H_{79}N_4O_9P_3Zn$); $\lambda_{abs}$=427, 555, 601 nm.

Zn(II)-5-[4-[1,1,1-Tris[4-(dihydroxyphosphorylmethyl)phenyl]methyl]phenyl]-10,15,20-tri-p-tolylporphyrin (Zn46). A solution of Zn44 (33 mg, 23.4 μmol) in $CHCl_3$ (2.3 mL) was treated with TEA (65 μL, 470 μmol) and TMS—Br (46 μL, 350 μmol) and the mixture was refluxed under argon. After 2 h, the solution was cooled and $CHCl_3$ (10 mL) and water (10 mL) were added. The porphyrin preferentially dissolved in the aqueous layer. The mixture was concentrated. The solid was suspended in hexanes, sonicated for 10 min, and centrifuged. The supernatant was decanted. This process was repeated once. The solid was dissolved in methanol with sonication. The solution was poured into diethyl ether and the precipitate was collected to afford a purple solid (24 mg, 82%): FABMS obsd 1242.2656, calcd 1242.2630 ($C_{69}H_{57}N_4O_9P_3Zn$); $\lambda_{abs}$=423, 522, 558, 599 nm.

REFERENCES (1) Li, Q.; Surthi, S.; Mathur, G.; Gowda, S.; Sorenson, T. A.; Tenent, R. C.; Kuhr, W. G.; Tamaru, S.-I.; Lindsey, J. S.; Liu, Z.; Bocian, D. F.; Misra, V. *Appl. Phys. Lett.* 2003, 83, 198-200.
(2) Ungashe, S. B.; Wilson, W. L.; Katz, H. E.; Scheller, G. R.; Putvinski, T. M. *J. Am. Chem. Soc.* 1992, 114, 8717-8719.
(3) Katz, H. E. *Chem. Mater.* 1994, 6, 2227-2232.
(4) Deniaud, D.; Schöllorn, B.; Mansuy, D.; Rouxel, J.; Battioni, P.; Bujoli, B. *Chem. Mater.* 1995, 7, 995-1000.
(5) Deniaud, D.; Spyroulias, G. A.; Bartoli, J.-F.; Battioni, P.; Mansuy, D.; Pinel, C.; Odobel, F.; Bujoli, B. *New J. Chem.* 1998, 901-905.
(6) Nixon, C. M.; Le Claire, K.; Odobel, F.; Bujoli, B.; Talham, D. R. *Chem. Mater.* 1999, 11, 965-976.
(7) Buehler, J. W.; Simon, J. R. *Eur. J. Inorg. Chem.* 2000, 2615-2621.
(8) Král, V.; Rusin, O.; Charvátová, J.; Anzenbacher, P. Jr.; Fogl, J. *Tetrahedron Lett.* 2000, 41, 10147-10151.
(9) Wedel, M.; Walter, A.; Montforts, F.-P. *Eur. J. Org. Chem.* 2001, 1681-1687.
(10) Rusin, O.; Hub, M.; Král, V. *Mater. Sci. Eng. C* 2001, 18, 135-140.
(11) Charvátová, J.; Rusin, O.; Král, V.; Volka, K.; Matêjka, P. *Sensors Acuators B* 2001, 76, 366-372.
(12) (a) Wightman, M. D.; M. S. Thesis, Northwestern University, June 2001. (b) Massari, A. M.; Gurney, R. W.; Wightman, M. D.; Huang, C.-H. K.; Nguyen, S. B.; Hupp, J. T. *Polyhedron* 2003, 22, 3065-3072.
(13) Benitez, I. O.; Bujoli, B.; Camus, L. J.; Lee, C. M.; Odobel, F.; Talham, D. R. *J. Am. Chem. Soc.* 2002, 124, 4363-4370.
(14) Chng, L. L.; Chang, C. J.; Nocera, D. G. *Org. Lett.* 2003, 5, 2421-2424.
(15) Buehler, J. W. In *Porphyrins and Metalloporphyrins; Smith,* K. M. Ed.; Elsevier Scientific Publishing Co.: Amsterdam 1975, pp. 157-231.
(16) (a) Roth, K. M.; Dontha, N.; Dabke, R. B.; Gryko, D. T.; Clausen, C.; Lindsey, J. S.; Bocian, D. F.; Kuhr, W. G. *J. Vac. Sci. Technol. B.* 2000, 18, 2359-2364. (b) Roth, K. M.; Gryko, D. T.; Clausen, C.; Li, J.; Lindsey, J. S.; Kuhr, W. G.; Bocian, D. F. *J. Phys. Chem. B* 2002, 106, 8639-8648.
(17) Whitesell, J. K.; Chang, H. K. *Science* 1993, 261, 73-76.
(18) Nierengarten, J.-F.; Habicher, T.; Kessinger, R.; Cardullo, F.; Diederich, F.; Gramlich, V.; Gisselbrecht, J.-P.; Boudon, C.; Gross, M. *Helv. Chim. Acta* 1997, 80, 2238-2276.
(19) Fox, M. A.; Whitesell, J. K.; McKerrow, A. J. *Langmuir* 1998, 14, 816-820.
(20) Fox, M. A.; Li, W.; Wooten, M.; McKerrow, A.; Whitesell, J. K. *Thin Solid Films* 1998, 327-329, 477-480.
(21) Wang, Y.; Cardona, C. M.; Kaifer, A. E. *J. Am. Chem. Soc.* 1999, 121, 9756-9757.
(22) Hu, J.; Mattern, D. L. *J. Org. Chem.* 2000, 65, 2277-2281.
(23) Siiman, O.; Burshteyn, A.; Maples, J. A.; Whitesell, J. K. *Bioconjugate Chem.* 2000, 11, 549-556.
(24) Zhu, L.; Tang, H.; Harima, Y.; Yamashita, K.; Hirayama, D.; Aso, Y.; Otsubo, T. *Chem. Commun.* 2001, 1830-1831.
(25) Otsubo, T.; Aso, Y.; Takimiya, K. *J. Mater. Chem.* 2002, 12, 2565-2575.
(26) Galoppini, E.; Guo, W.; Zhang, W.; Hoertz, P. G.; Qu, P.; Meyer, G. J. *J. Am. Chem. Soc.* 2002, 67, 7801-7811.
(27) Hirayama, D.; Takimiya, K.; Aso, Y.; Otsubo, T.; Hasobe, T.; Yamada, H.; Imahori, H.; Fukuzumi, S.; Sakata, Y. *J. Am. Chem. Soc.* 2002, 124, 532-533.
(28) Nikitin, K.; Long, B.; Fitzmaurice, D. *Chem. Commun.* 2003, 282-283.
(29) Long, B.; Nikitin, K.; Fitzmaurice, D. *J. Am. Chem. Soc.* 2003, 125, 5152-5160.
(30) Zhu, L.; Tang, H.; Harima, Y.; Yamashita, K.; Aso, Y.; Otsubo, T. *J. Mater. Chem.* 2002, 12, 2250-2254.
(31) Yao, Y.; Tour, J. M. *J. Org. Chem.* 1999, 64, 1968-1971.
(32) Galoppini, E.; Guo, W.; Qu, P.; Meyer, G. J. *J. Am. Chem. Soc.* 2001, 123, 4342-4343.
(33) Guo, W.; Galoppini, E.; Rydja, G.; Pardi, G. *Tetrahedron Lett.* 2000, 41, 7419-7421.
(34) Kittredge, K. W.; Minton, M. A.; Fox, M. A.; Whitesell, J. K. *Helv. Chim. Acta* 2002, 85, 788-798.
(35) Li, Q.; Rukavishnikov, A. V.; Petukhov, P. A.; Zaikova, T. O.; Jin, C.; Keana, J. F. W. *J. Org. Chem.* 2003, 68, 4862-4869.
(36) Hong, B. J.; Shim, J. Y.; Oh, S. J.; Park, J. W. *Langmuir* 2003, 19, 2357-2365.
(37) McKenna, C. E.; Higa, M. T.; Cheung, N. H.; McKenna, M.-C. *Tetrahedron Lett.* 1977, 155-158.
(38) Kamber, M.; Just, G. *Can. J. Chem.* 1985, 63, 823-827.
(39) Berkowitz, D. B.; Sloss, D. G. *J. Org. Chem.* 1995, 60, 7047-7050.
(40) Gardner, T. J.; Frisbie, C. D.; Wrighton, M. S. *J. Am. Chem. Soc.* 1995, 117, 6927-6933.
(41) Alley, S. R.; Henderson, W. *J. Organomet. Chem.* 2001, 637-639, 216-229.
(42) Kim, Y.-C.; Brown, S. G.; Harden, T. K.; Boyer, J. L.; Dubyak, G.; King, B. F.; Burnstock, G.; Jacobson, K. A. *J. Med. Chem.* 2001, 44, 340-349.
(43) Liu, D.-G.; Wang, X.-Z.; Gao, Y.; Li, B.; Yang, D.; Burke, T. R., Jr. *Tetrahedron* 2002, 58, 10423-10428.
(44) Rabinowitz, R. *J. Org. Chem.* 1963, 28, 2975-2978.
(45) Sekine, M.; Iimura, S.; Nakanishi, T. *Tetrahedron Lett.* 1991, 32, 395-398.
(46) Clerici, A.; Pastori, N.; Porta, O. *Tetrahedron* 1998, 54, 15679-15690.
(47) Lindsey, J. S.; Prathapan, S.; Johnson, T. E.; Wagner, R. W. *Tetrahedron* 1994, 50, 8941-8968.
(48) Lindsey, J. S.; Wagner, R. W. *J. Org. Chem.* 1989, 54, 828-836.
(49) Lindsey, J. S.; Woodford, J. N. *Inorg. Chem.* 1995, 34, 1063-1069.
(50) O'Shea, D. F.; Miller, M. A.; Matsueda, H.; Lindsey, J. S. *Inorg. Chem.* 1996, 35, 7325-7338.
(51) Littler, B. J.; Miller, M. A.; Hung, C.-H.; Wagner, R. W.; O'Shea, D. F.; Boyle, P. D.; Lindsey, J. S. *J. Org. Chem.* 1999, 64, 1391-1396.
(52) Rao, P. D.; Dhanalekshmi, S.; Littler, B. J.; Lindsey, J. S. *J. Org. Chem.* 2000, 65, 7323-7344.
(53) Geier, G. R., III; Callinan, J. B.; Rao, P. D.; Lindsey, J. S. *J. Porphyrins Phthalocyanines* 2001, 5, 810-823.
(54) Rao, P. D.; Littler, B. J.; Geier, G. R., III; Lindsey, J. S. *J. Org. Chem.* 2000, 65, 1084-1092.
(55) Taniguchi, M.; Ra, D.; Mo, G.; Balasubramanian, T.; Lindsey, J. S. *J. Org. Chem.* 2001, 66, 7342-7354.
(56) Ravikanth, M.; Strachan, J.-P.; Li, F.; Lindsey, J. S. *Tetrahedron* 1998, 54, 7721-7734.
(57) Yu, L.; Lindsey, J. S. *J. Org. Chem.* 2001, 66, 7402-7419.
(58) Wagner, R. W.; Ciringh, Y.; Clausen, C.; Lindsey, J. S. *Chem. Mater.* 1999, 11, 2974-2983.
(59) Wagner, R. W.; Johnson, T. E.; Lindsey, J. S. *J. Am. Chem. Soc.* 1996, 118, 11166-11180.
(60) (a) Fenyo, D.; Chait, B. T.; Johnson, T. E.; Lindsey, J. S. *J. Porphyrins Phthalocyanines* 1997, 1, 93-99. (b) Srinivasan, N.; Haney, C. A.; Lindsey, J. S.; Zhang, W.; Chait, B. T. *J. Porphyrins Phthalocyanines* 1999, 3, 283-291.
(61) Wagner, R. W.; Li, F.; Du, H.; Lindsey, J. S. *Org. Process Res. Dev.* 1999, 3, 28-37.

(62) Wen, L.; Li, M.; Schlenoff, J. B. *J. Am. Chem. Soc.* 1997, 119, 7726-7733.
(63) (a) MUrtensson, J.; Sandros, K.; Wennerström, O. *Tetrahedron Lett.* 1993, 34, 541-544. (b) Jiang B.; Jones, W. E., Jr. *Macromolecules* 1997, 30, 5575-5581. (c) Král, V.; Cattani, A.; Sinica, A.; Schmidtchen, F. P. *Tetrahedron* 1999, 55, 7829-7834. (d) Buehler, J. W.; Simon, J. R. *Eur. J. Inorg. Chem.* 2000, 2615-2621. (e) Salom-Roig, X. J.; Chambron, J.-C.; Goze, C.; Heitz, V.; Sauvage, J.-P. *Eur. J. Org. Chem.* 2002, 3276-3280.
(64) Gryko, D.; Lindsey, J. S. *J. Org. Chem.* 2000, 65, 2249-2252.
(65) Gryko, D.; Li, J.; Diers, J. R.; Roth, K. M.; Bocian, D. F.; Kuhr, W. G.; Lindsey, J. S. *J. Mater. Chem.* 2001, 11, 1162-1180.
(66) Kadish, K. M.; Van Caemelbecke, E.; Royal, G. In *The Porphyrin Handbook; Kadish, K. M., Smith, K. M., Guilard, R., Eds.; Academic Press: San Diego, Calif.*, 2000; Vol. 8, pp 1-114.
(67) Laha, J. K.; Dhanalekshmi, S.; Taniguchi, M.; Ambroise, A.; Lindsey, J. S. *Org. Process Res. Dev.* 2003, 7, Web Edition.
(68) Cho, W.-S.; Kim, H.-J.; Littler, B. J.; Miller, M. A.; Lee, C.-H.; Lindsey, J. S. *J. Org. Chem.* 1999, 64, 7890-7901.

The foregoing is illustrative of the present invention, and is not to be construed as limiting thereof. The invention is defined by the following claims, with equivalents of the claims to be included therein.

We claim:

1. A method of making a chlorin, comprising:
   reducing a 9-halo, 5-phosphono, 1-acyldipynomethane to produce a first reaction product; and then
   reacting said first reaction product with a western half to produce said chlorin; wherein said phosphono is selected from the group consisting of dialkyl phosphono, diaryl phosphono, and dialkylaryl phosphono.

2. The method of claim 1, wherein said halo is selected from the group consisting of chloro, bromo and iodo.

3. The method of claim 1, wherein said phosphono is coupled to said dipyrromethane by a linking group.

4. The method of claim 3, wherein said linking group is selected from the group consisting of alkyl, aryl, alkylaryl, and alkylarylalkyl groups.

* * * * *

UNITED STATES PATENT AND TRADEMARK OFFICE
CERTIFICATE OF CORRECTION

PATENT NO. : 8,278,439 B2  
APPLICATION NO. : 13/299894  
DATED : October 2, 2012  
INVENTOR(S) : Lindsey et al.

It is certified that error appears in the above-identified patent and that said Letters Patent is hereby corrected as shown below:

In the Specification:

Column 17, Scheme 7: Please correct

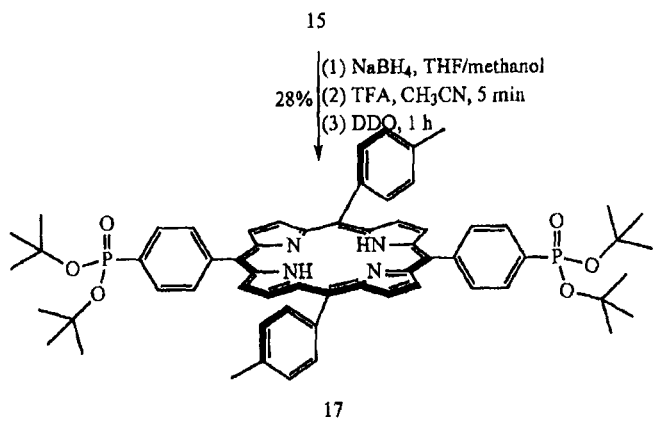

....to read

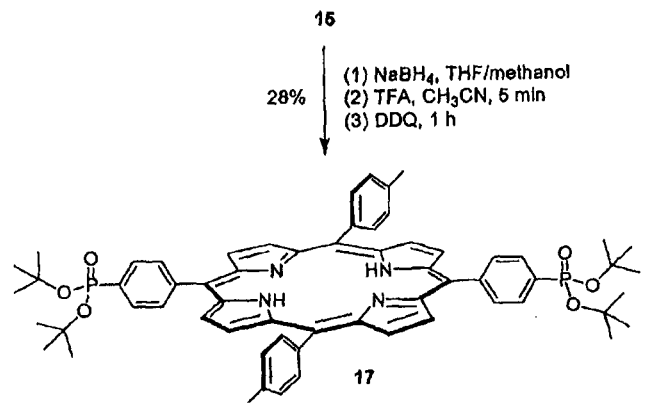

Signed and Sealed this  
Fourth Day of February, 2014

Michelle K. Lee  
*Deputy Director of the United States Patent and Trademark Office*

CERTIFICATE OF CORRECTION (continued)
U.S. Pat. No. 8,278,439 B2

Columns 19 – 20, Scheme 9, Dyad-1: Please correct

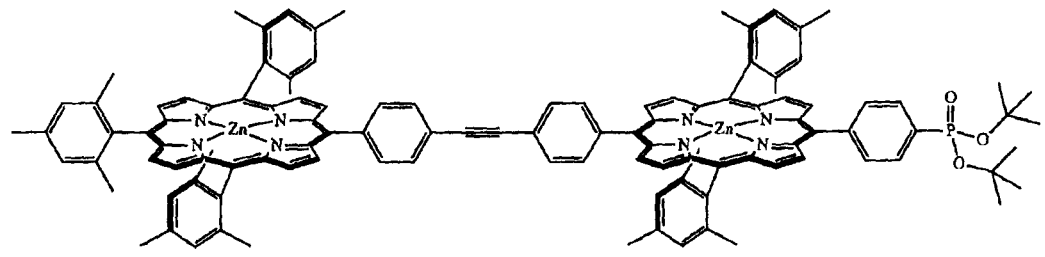

....to read

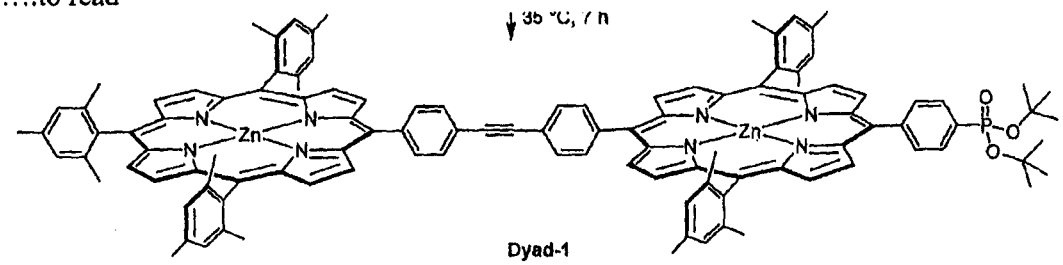

....and, Dyad-2: Please correct

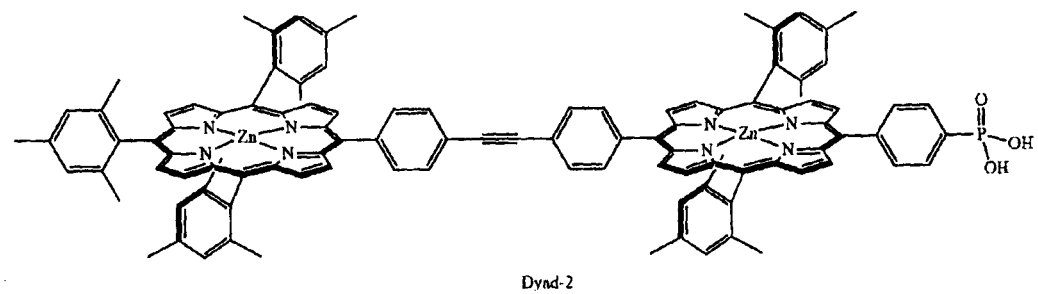

....to read

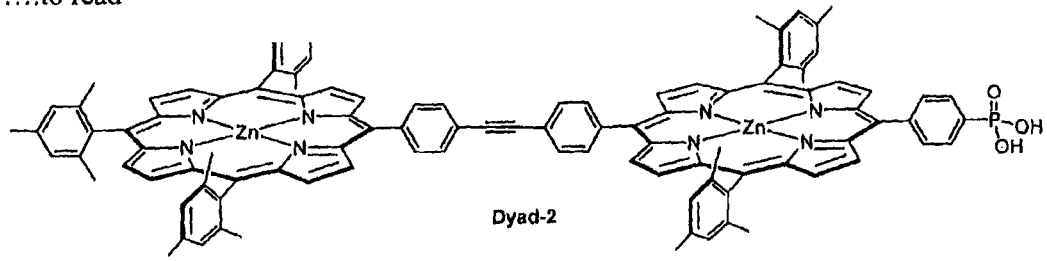

CERTIFICATE OF CORRECTION (continued)
U.S. Pat. No. 8,278,439 B2

Column 25, Scheme 14, Co24: Please correct

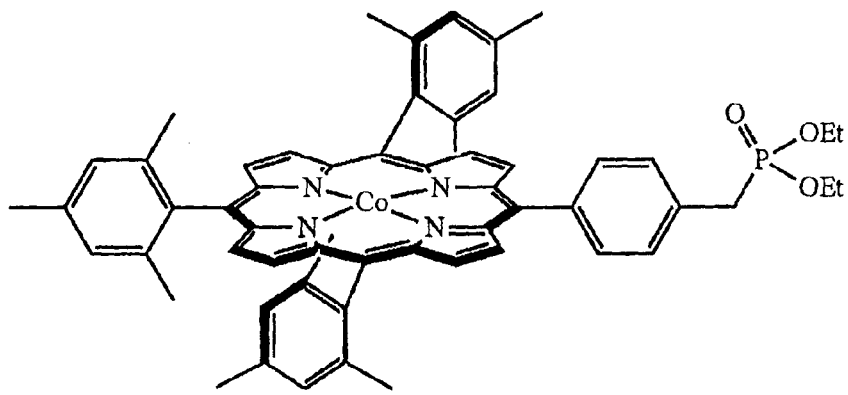

....to read

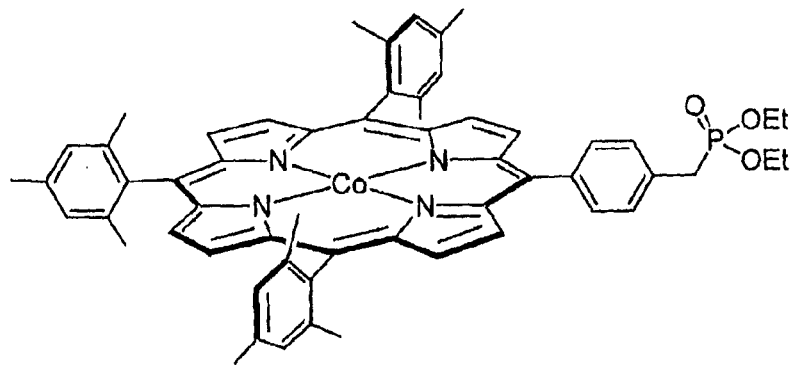

Scheme 14, Co25: Please correct

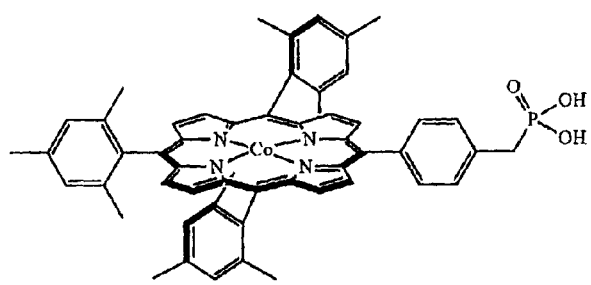

....to read

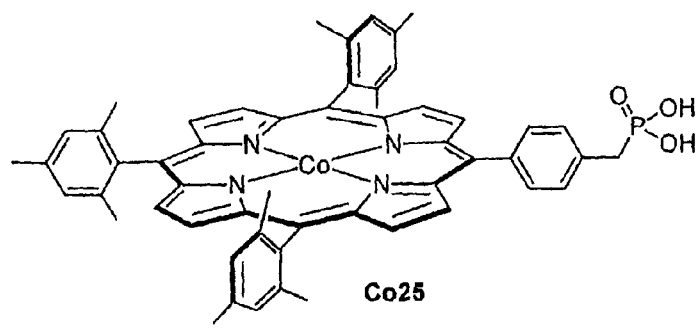

CERTIFICATE OF CORRECTION (continued)
U.S. Pat. No. 8,278,439 B2

Column 34, Line 27: Please correct "1.94 mmol) were coupled"
                to read -- 1.94 µmol) were coupled --
    Line 35: Please correct "tert-Bu)$^{+]}$, 935.6"
                to read -- tert-Bu)$^{+}$], 935.6 --

Column 41, References, Line 23: Please correct "(7) Buehler, J. W.; Simon, J. R."
                to read -- (7) Buchler, J.W.; Simon, J. R. --

Column 43, References, Line 3: Please correct "(63) (a) M∪rterason, J.; Sandros, K.;"
                to read -- (63) (a) Mårtensson, J.; Sandros, K.; --